(12) United States Patent
Onda et al.

(10) Patent No.: US 11,185,450 B2
(45) Date of Patent: Nov. 30, 2021

(54) ABSORBENT ARTICLE

(71) Applicant: KAO CORPORATION, Tokyo (JP)

(72) Inventors: Aiko Onda, Utsunomiya (JP); Ryota Kuramae, Utsunomiya (JP)

(73) Assignee: KAO CORPORATION, Tokyo (JP)

( * ) Notice: Subject to any disclaimer, the term of this patent is extended or adjusted under 35 U.S.C. 154(b) by 404 days.

(21) Appl. No.: 16/474,325

(22) PCT Filed: Dec. 6, 2017

(86) PCT No.: PCT/JP2017/043863
§ 371 (c)(1),
(2) Date: Jun. 27, 2019

(87) PCT Pub. No.: WO2018/123488
PCT Pub. Date: Jul. 5, 2018

(65) Prior Publication Data
US 2019/0336355 A1      Nov. 7, 2019

(30) Foreign Application Priority Data
Dec. 28, 2016   (JP) .............................. JP2016-255098

(51) Int. Cl.
*A61F 13/532*       (2006.01)
*A61F 13/535*       (2006.01)
(Continued)

(52) U.S. Cl.
CPC .......... *A61F 13/532* (2013.01); *A61F 13/535* (2013.01); *A61F 13/539* (2013.01);
(Continued)

(58) Field of Classification Search
CPC .... A61F 13/532; A61F 13/535; A61F 13/539; A61F 13/5323; A61F 2013/530554; A61F 2013/53908; A61F 2013/4568
See application file for complete search history.

(56) References Cited

U.S. PATENT DOCUMENTS 10,052,242  B2 *   8/2018   Bianchi ................. A61F 13/539
10,441,481  B2 *  10/2019   Bianchi ................. A61F 13/534
(Continued)

FOREIGN PATENT DOCUMENTS

CN         101018528 A       8/2007
EP         0 293 208 A1     11/1988
(Continued)

OTHER PUBLICATIONS

International Search Report (PCT/ISA/210) issued in PCT/JP2017/043863, dated Mar. 13, 2018.

*Primary Examiner* — Susan S Su
(74) *Attorney, Agent, or Firm* — Birch, Stewart, Kolasch & Birch, LLP

(57) ABSTRACT

A diaper (10) includes an absorbent assembly (20) including a topsheet (21), a backsheet (22), and an absorbent core (24), and has an article longitudinal direction (X) and an article lateral direction (Y). The absorbent core (24) is formed of a sheet-like article (1) including a plurality of absorbent units (4), each including a long base portion (2) and water-absorbent polymer particles (3). The sheet-like article (1) includes a plurality of unit portions arranged in the longitudinal direction (x1 direction), each unit portion including a plurality of the absorbent units (4) arranged side by side in the lateral direction (y1 direction). The sheet-like article (1) includes a pair of longitudinal joined regions (41, 41), a pair of lateral joined regions (42, 42), and intermediate lateral joined regions (43, 43). The sheet-like article (1) is joined to a constituent member adjacent thereto in the thickness direction (Z) at the pair of longitudinal joined regions (41, 41), the pair of lateral joined regions (42, 42), and the intermediate lateral joined regions (43, 43). Each unit portion includes a section in which neither the upper side nor (Continued)

the lower side thereof in the thickness direction (Z) is joined to the constituent member.

20 Claims, 10 Drawing Sheets

(51) Int. Cl.
*A61F 13/539* (2006.01)
*A61F 13/49* (2006.01)
*A61F 13/53* (2006.01)
*A61F 13/45* (2006.01)

(52) U.S. Cl.
CPC ....... *A61F 13/49* (2013.01); *A61F 2013/4568* (2013.01); *A61F 2013/530554* (2013.01); *A61F 2013/53908* (2013.01)

(56) References Cited

U.S. PATENT DOCUMENTS

| | | |
|---|---|---|
| 2004/0127874 A1 | 7/2004 | Nishizawa et al. |
| 2006/0206091 A1 | 9/2006 | Cole et al. |
| 2007/0142802 A1* | 6/2007 | Suzuki ................ A61F 13/5323 604/368 |
| 2011/0208147 A1* | 8/2011 | Kawakami .......... A61F 13/5323 604/372 |
| 2012/0035565 A1* | 2/2012 | Okawa .................. A61F 13/505 604/372 |
| 2012/0226253 A1* | 9/2012 | Urushihara ........... A61F 13/539 604/372 |
| 2014/0142531 A1 | 5/2014 | Sasayama et al. |
| 2015/0144270 A1* | 5/2015 | Nakakado ......... A61F 13/15658 156/580.2 |
| 2015/0173980 A1* | 6/2015 | Umebayshi ........... B29C 66/232 604/367 |

FOREIGN PATENT DOCUMENTS

| | | |
|---|---|---|
| JP | 63-18122 U | 2/1988 |
| JP | 1-87720 U | 6/1989 |
| JP | 2000-102562 A | 4/2000 |
| JP | 2002-224162 A | 8/2002 |
| JP | 2002-315777 A | 10/2002 |
| JP | 2004-121390 A | 4/2004 |
| JP | 2004-223065 A | 8/2004 |
| JP | 2010-104523 A | 5/2010 |
| JP | 2013-5997 A | 1/2013 |
| JP | 2013-39804 A | 2/2013 |
| RU | 128 104 U1 | 5/2013 |

* cited by examiner

ABSORBENT ARTICLE

TECHNICAL FIELD

The present invention relates to an absorbent article such as a disposable diaper.

BACKGROUND ART

There are conventionally known absorbent articles, such as disposable diapers, sanitary napkins, and incontinence pads, wherein an absorbent member employed in the absorbent article is provided with a plurality of slits, to thereby improve the softness of the absorbent member and reduce thickness (see Patent Literature 1).

As another technique, Patent Literature 2 discloses an absorbent article using an absorbent core formed only of water-absorbent polymer particles.

CITATION LIST

Patent Literature

Patent Literature 1: Japanese Utility Model Application Laid-Open Publication JP S63-18122U
Patent Literature 2: Japanese Patent Application Laid-Open Publication JP 2013-5997A

SUMMARY OF INVENTION

The invention relates to an absorbent article that includes an absorbent assembly including a topsheet, a backsheet, and an absorbent core interposed between the topsheet and the backsheet, the absorbent article having an article longitudinal direction extending from a front region to be arranged on a front side of a wearer toward a rear region to be arranged on a rear side of the wearer, and an article lateral direction orthogonal to the article longitudinal direction. The absorbent core is formed of a sheet-like article including a plurality of absorbent units, each of the plurality of absorbent units including: a long base portion having a lateral direction, a longitudinal direction that is longer than the lateral direction, and a thickness direction; and water-absorbent polymer particles that are fixed to a surface of at least one face of the long base portion. The absorbent units are arranged such that the absorbent unit's longitudinal direction is oriented in the article longitudinal direction. The sheet-like article includes a plurality of unit portions arranged in the longitudinal direction, each of the plurality of unit portions including a plurality of the absorbent units arranged side by side in the lateral direction. The sheet-like article includes: a pair of longitudinal joined regions extending in the longitudinal direction at respective lateral sides which are along the longitudinal direction; a pair of lateral joined regions extending in the lateral direction at respective end portions in the longitudinal direction; and an intermediate lateral joined region extending in the lateral direction between the lateral joined regions. The sheet-like article is joined at the longitudinal joined regions, the lateral joined regions, and the intermediate lateral joined region to a constituent member that constitutes the absorbent article and that is adjacent on at least either an upper side or a lower side in the thickness direction, and each of the unit portions includes a section in which neither the upper side nor the lower side thereof in the thickness direction is joined to the constituent member.

DESCRIPTION OF EMBODIMENTS

Patent Literature 1, however, merely describes an absorbent member provided with a plurality of slits. Thus, in the absorbent article disclosed in Patent Literature 1, the absorbent member tends to gather toward the center when an external force is applied inwardly, in the width direction, from the wearer's legs when the absorbent article is worn, which may result in giving an uncomfortable feel to the wearer wearing the absorbent article. Further, the absorbent material of the absorbent member which has gathered toward the center does not easily return to its original position, which may become a cause of leakage.

Patent Literature 2 merely describes an absorbent core made only of water-absorbent polymer particles, and describes nothing about forming slits in the absorbent core.

The present invention relates to an absorbent article capable of overcoming the aforementioned drawbacks of the conventional art.

Figure 1:
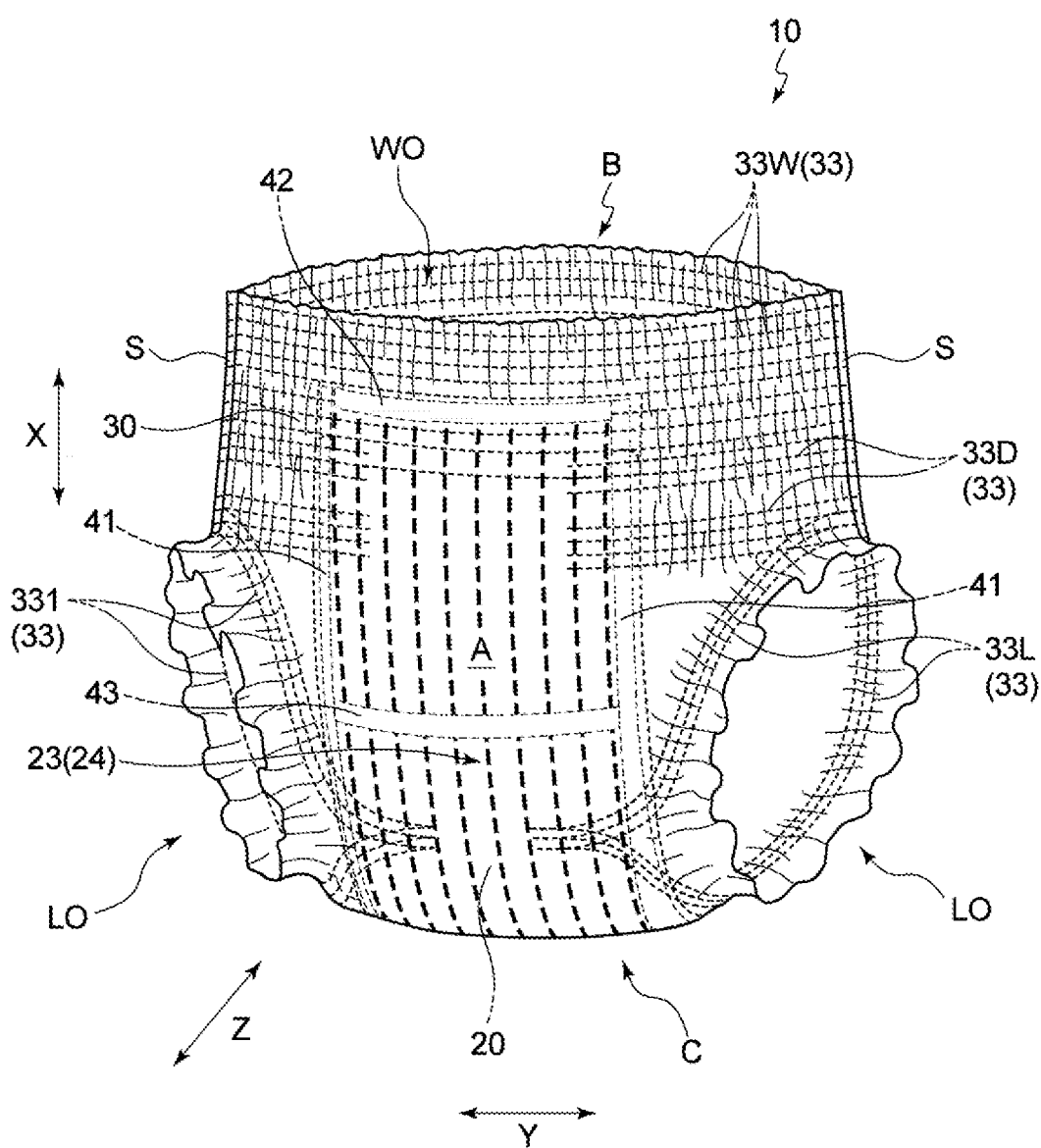
FIG. 1 is a perspective view of a pull-on disposable diaper which is an embodiment of an absorbent article of the invention.
Figure 2:
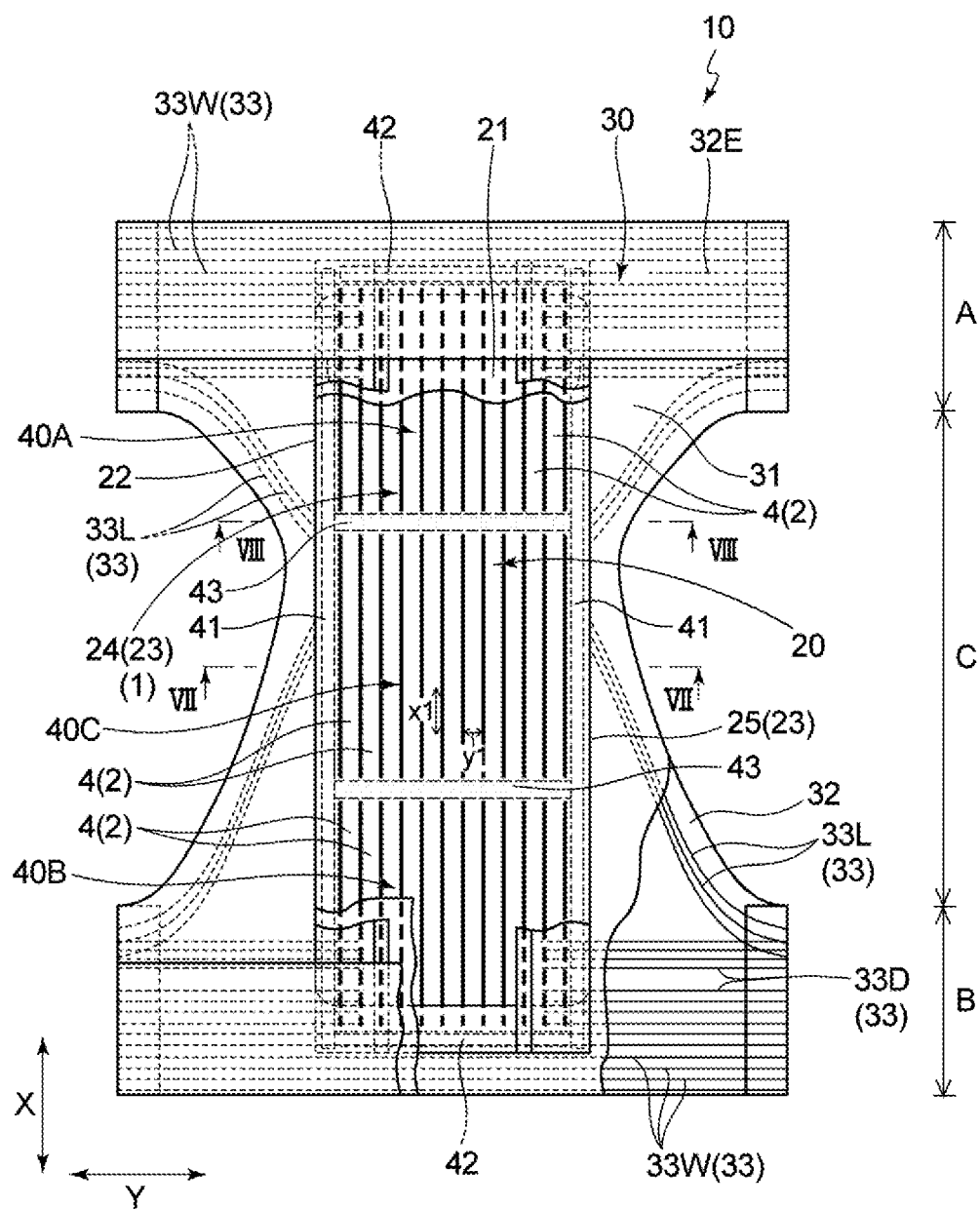
FIG. 2 is a partially cutaway plan view illustrating the diaper of FIG. 1 in a stretched and spread out state.

The invention is described below according to preferred embodiments thereof with reference to the drawings. FIG. 1 illustrates a perspective view of a natural state of a disposable diaper 10 (also referred to hereinafter simply as "diaper 10") which is an embodiment of an absorbent article of the invention. FIG. 2 is a partially cutaway plan view illustrating the diaper 10 of FIG. 1 in a stretched and spread out state.

As illustrated in FIGS. 1 and 2, the diaper 10 is a so-called pull-on disposable diaper. The diaper 10 includes an absorbent assembly 20 including a topsheet 21, a backsheet 22, and an absorbent core 24 interposed between the topsheet 21 and the backsheet 22, and has an article longitudinal direction X extending from a front region to be arranged on a front side of a wearer toward a rear region to be arranged on a rear side of the wearer, and an article lateral direction Y orthogonal to the article longitudinal direction X. Preferably, the diaper 10 includes the absorbent assembly 20, and an outer cover 30 located on the non-skin-facing surface side of the absorbent assembly 20 and to which the absorbent assembly 20 is fixed.

As illustrated in FIG. 2, the diaper 10 is divided into: a front region A to be arranged on the wearer's front side when worn; a rear region B to be arranged on the wearer's rear side; and a crotch region C located therebetween. The crotch region C is a region where the outer cover 30's both lateral side edges, which are along the article longitudinal direction X, are narrowed inward in the article lateral direction Y, and is arranged in the wearer's crotch region when the diaper 10 is worn. The front region A is a region located more toward the wearer's front side than the crotch region C when the diaper 10 is worn. The rear region B is a region located more toward the wearer's rear side than the crotch region C when the diaper 10 is worn. The diaper 10 has a thickness direction Z in its thickness direction.

In the present Description, the "skin-facing surface side" refers to the side (face), of the front and rear sides (faces) of each member of the diaper 10, that is arranged on the wearer's skin side when the diaper 10 is worn. The "non-skin-facing surface side" refers to the side (face), of the front and rear sides (faces) of each member of the diaper 10, that is arranged on the opposite side from the wearer's skin side when the diaper 10 is worn. Further, in the following explanation, the "article longitudinal direction X" refers to the direction extending from the front region A to the rear region B in the diaper 10 in a stretched and spread out state. The "article lateral direction Y" is the direction orthogonal to the article longitudinal direction X of the diaper 10 in a stretched and spread out state, and refers to the width direction of the diaper 10 in a stretched and spread out state.

As illustrated in FIG. 2, in the diaper 10, the absorbent assembly 20 has a rectangular shape that is oblong in longitudinal direction, and is joined to a central area, in the article lateral direction Y, of the outer cover 30 by a known joining means, such as a hot-melt adhesive, in a manner that the absorbent assembly 20 extends from the front region A up to the rear region B with the absorbent assembly's article longitudinal direction X matching the diaper 10's article longitudinal direction X. The outer cover 30's both lateral side edge portions in a section located in the front region A are joined together with the outer cover's respective lateral side edge portions in a section located in the rear region B by a known joining means such as heat sealing, ultrasonic sealing, or the like. Thus, a pair of side seals S, S is formed in the diaper 10. This joining also forms, in the diaper 10, a waist opening WO and a pair of leg openings LO, LO as illustrated in FIG. 1, and the outer cover 30 is thus formed into a three-dimensional pull-on shape.

As illustrated in FIG. 2, in the diaper 10, the outer cover 30 includes an inner sheet 31 and an outer sheet 32. The inner sheet 31 and the outer sheet 32 have the same shape in the article lateral direction Y. In the article longitudinal direction X, however, the outer sheet 32 extends out from the front and rear end portions of the inner sheet 31, and the extension portions 32E cover the respective front and rear end regions, in the article longitudinal direction X, of the absorbent assembly 20. The outer edge of the outer cover 30 constitutes the contour of the spread-out diaper 10.

As illustrated in FIGS. 1 and 2, in the diaper 10, elastic members 33 are fixed between the inner sheet 31 of the outer cover 30 and the outer sheet 32 of the outer cover 30.

Preferably, in the diaper 10, the elastic members 33 include: waist elastic members 33W that are arranged between the inner sheet 31 and the outer sheet 32 and that form waist gathers in the peripheral edge section of the waist opening WO; leg elastic members 33L that form leg gathers in the peripheral edge section of each leg opening LO; and below-waist elastic members 33D that form below-waist gathers in a below-waist portion (a region from a position 20 mm below the peripheral edge of the waist opening WO to the upper end of the leg openings LO). The waist elastic members 33W, the leg elastic members 33L, and the below-waist elastic members 33D are joined and fixed in their stretched state by a joining means such as a hot-melt adhesive.

Figure 3:
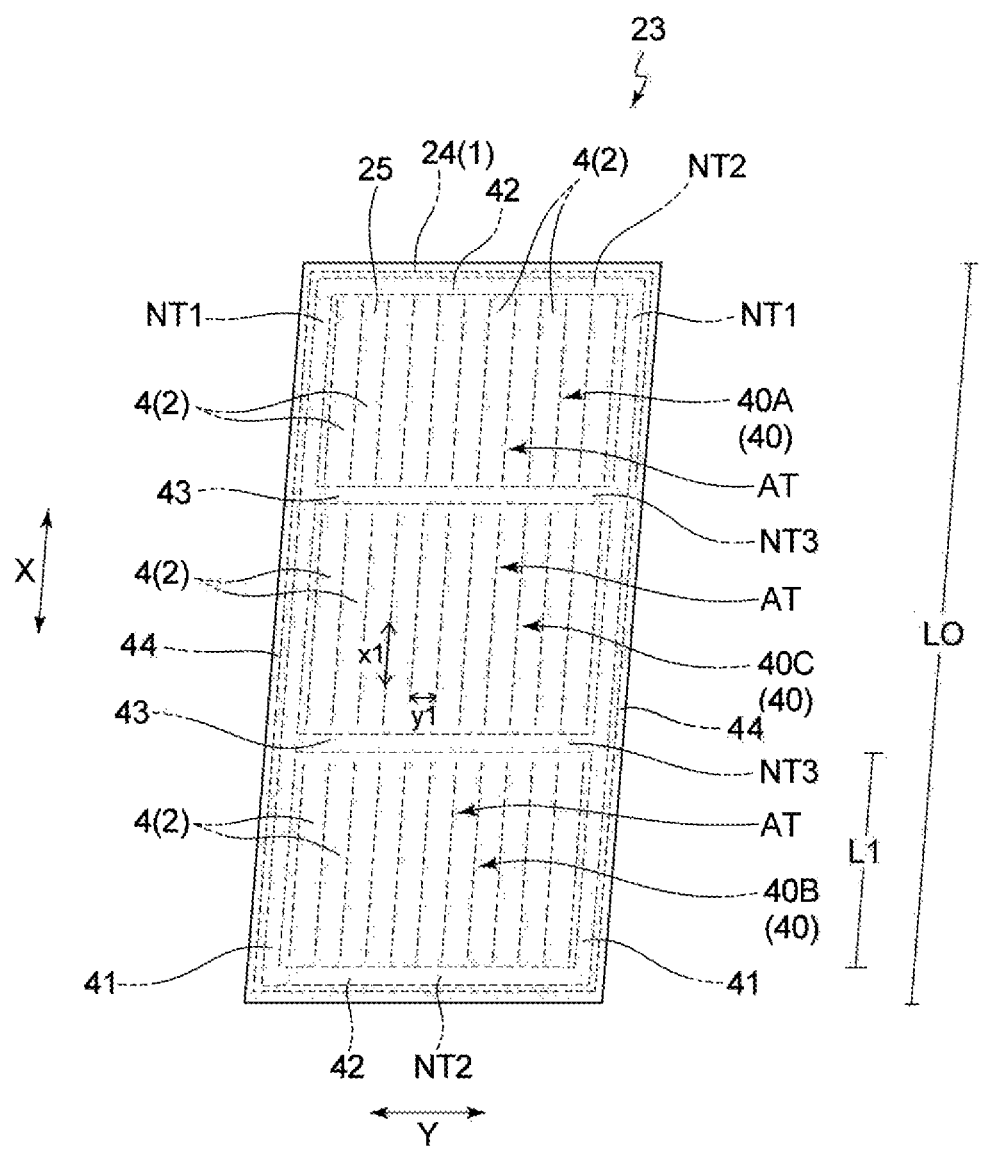
FIG. 3 is a perspective view illustrating an absorbent member of the diaper illustrated in FIG. 1.
Figure 4:
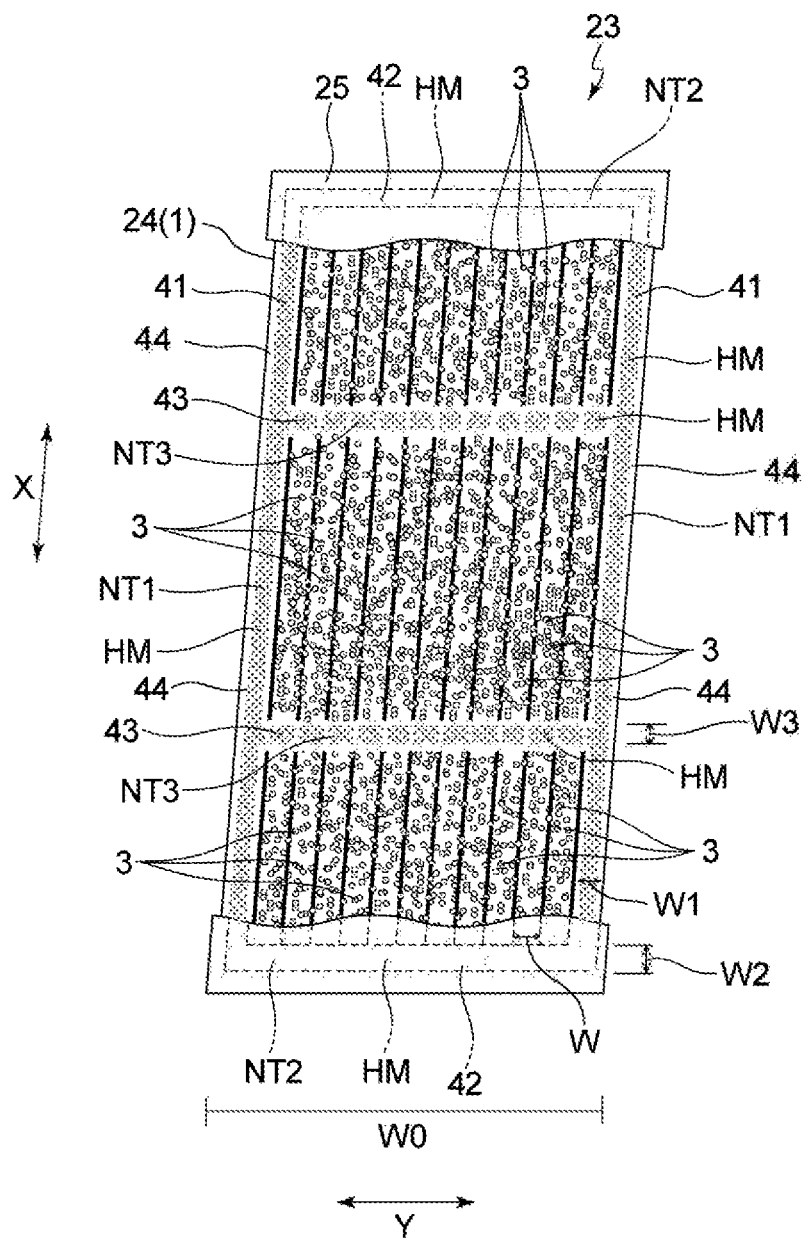
FIG. 4 is a perspective view in which a core-wrap sheet of the absorbent member illustrated in FIG. 3 is partially cutaway.

As illustrated in FIG. 2, in the diaper 10, the absorbent assembly 20 includes an absorbent member 23. As illustrated in FIGS. 3 and 4, the absorbent member 23 includes an absorbent core 24, and a liquid-permeable core-wrap sheet 25 that covers the absorbent core 24. As illustrated in FIGS. 3 and 4, in a planar view, the absorbent core 24 has a rectangular shape that is long in the article longitudinal direction X. The absorbent member 23 is formed by covering the entire absorbent core 24 with the core-wrap sheet 25. In the absorbent article, a so-called sublayer sheet may be arranged on at least one of the skin-facing surface and the non-skin-facing surface of the absorbent member 23.

Figure 5:
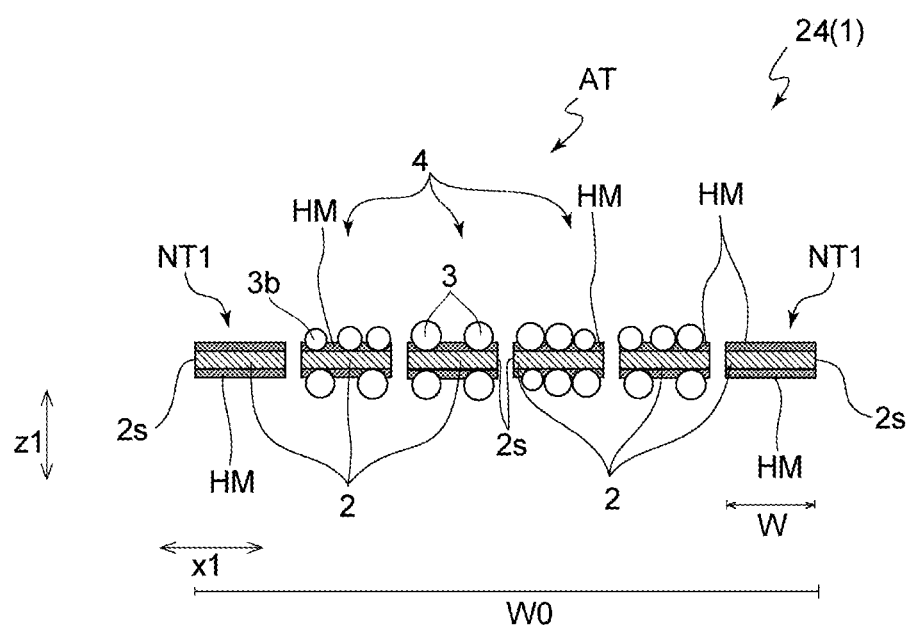
FIG. 5 is a cross-sectional view schematically illustrating an embodiment of a sheet-like article, which is an absorbent core of the absorbent member illustrated in FIG. 4, the figure illustrating a state before water-absorbent polymer particles absorb a liquid.
Figure 6:
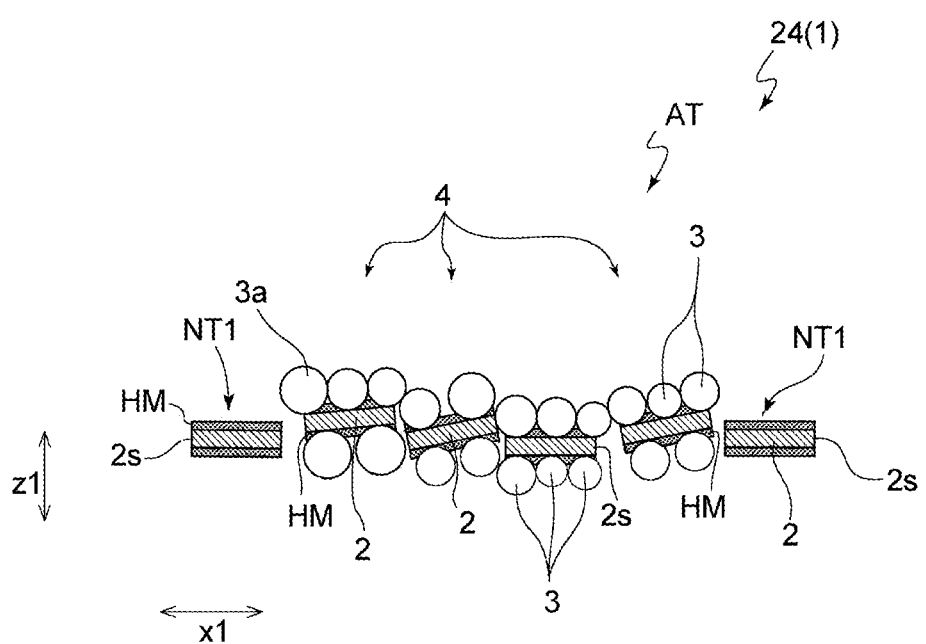
FIG. 6 is a cross-sectional view schematically illustrating a state in which the water-absorbent polymer particles in the sheet-like article illustrated in FIG. 5 have swollen by absorbing a liquid.

FIGS. 5 and 6 are cross-sectional views schematically illustrating a sheet-like article 1 which is the absorbent core 24. The sheet-like article 1 of FIG. 5 shows a state before water-absorbent polymer particles 3 absorb a liquid (also referred to hereinafter simply as "a state before use"). The sheet-like article 1 of FIG. 6 shows a state in which the water-absorbent polymer particles 3 have swollen by absorbing a liquid (also referred to hereinafter simply as "state after swelling"). Herein, a "state after swelling" refers to a state of the water-absorbent polymer particles 3 after immersing the sheet-like article 1 in a physiological saline solution (0.9 mass % sodium chloride aqueous solution), whose temperature has been adjusted to 25° C., for 60 minutes.

As illustrated in FIGS. 3 to 5, in the diaper 10, the absorbent core 24 is formed of the sheet-like article 1, which includes a plurality of the absorbent units 4, each absorbent unit 4 including: a long base portion 2 having a lateral direction (y1 direction), a longitudinal direction (x1 direction) that is longer than the lateral direction (y1 direction), and a thickness direction (z1 direction); and water-absorbent polymer particles 3 (also referred to hereinafter simply as "water-absorbent polymer 3") that are fixed to a surface of one face and the other face of the long base portion 2, wherein the absorbent units 4 are arranged such that the absorbent unit's longitudinal direction (x1 direction) is oriented in the article longitudinal direction X. Herein, the lateral direction (y1 direction), longitudinal direction (x1 direction), and thickness direction (z1 direction) of the long base portion 2 match the lateral direction (y1 direction), longitudinal direction (x1 direction), and thickness direction (z1 direction) of the absorbent unit 4, respectively. Note that, as illustrated in FIGS. 2 and 3, the sheet-like article 1, which forms the absorbent core 24, has a longitudinally-oblong rectangular shape that is long in the diaper 10's article longitudinal direction X and short in the diaper 10's article lateral direction Y in a planar view, and is arranged so as to extend from the front region A up to the rear region B with its longitudinal direction (x1 direction) matching the absorbent assembly 20's article longitudinal direction X or the diaper 10's article longitudinal direction X. The long base portion 2's thickness direction (z1 direction) and the absorbent unit 4's thickness direction (z1 direction) match the diaper 10's thickness direction Z.

As illustrated in FIGS. 3 and 4, in the diaper 10, the sheet-like article 1 forming the absorbent core 24 includes a plurality of unit portions 40 arranged in the longitudinal direction (x1 direction), each unit portion including a plurality of absorbent units 4 arranged side by side in the lateral direction (y1 direction). As an example of the plurality of unit portions 40 arranged in the longitudinal direction (x1 direction), the diaper 10 includes, in the sheet-like article 1, a front unit portion 40A arranged on the front region A side, a crotch unit portion 40C arranged in the crotch region C, and a rear unit portion 40B arranged on the rear region B side, the unit portions 40 being juxtaposed in the longitudinal direction (x1 direction). As illustrated in FIG. 4, in the diaper 10, the front unit portion 40A is a section arranged so as to extend from the front region A of the diaper 10 to the crotch region C's front region A side; and the rear unit portion 40B is a section that is arranged so as to extend from the crotch region C's rear region B side to the rear region B of the diaper 10. As described above, in the diaper 10, three unit portions 40 are juxtaposed in the longitudinal direction (x1 direction) in the sheet-like article 1 forming the absorbent core 24, and the unit portions 40 are arranged respectively in positions of the diaper 10's front region A, crotch region C, and rear region B.

The front unit portion 40A, the crotch unit portion 40C, and the rear unit portion 40B all have the same length in the lateral direction (y1 direction) and the same length in the longitudinal direction (x1 direction). Stated differently, in the sheet-like article 1, the front unit portion 40A, the crotch unit portion 40C, and the rear unit portion 40B, which are formed in the same shape, are juxtaposed in the longitudinal direction (x1 direction). Note, however, that, although the front unit portion 40A, the crotch unit portion 40C, and the rear unit portion 40B are formed in the same shape in the diaper 10, it is possible, for example, to make the length, in the longitudinal direction (x1 direction), of the crotch unit portion 40C longer than the length, in the longitudinal direction (x1 direction), of the front unit portion 40A and the rear unit portion 40B. The lengths, in the longitudinal direction (x1 direction), of the front unit portion 40A, the crotch unit portion 40C, and the rear unit portion 40B can be varied as appropriate. Further, the diaper 10 includes three unit portions (i.e., the front unit portion 40A, the crotch unit portion 40C, and the rear unit portion 40B) in the sheet-like article 1 forming the absorbent core 24, but the number of unit portions 40 to be arranged in the sheet-like article 1 can be varied as appropriate.

In the diaper 10, as illustrated in FIGS. 2 and 3, the unit portions 40 are arranged with a space therebetween in the longitudinal direction (x1 direction). Preferably, in the diaper 10, the front unit portion 40A, the crotch unit portion 40C, and the rear unit portion 40B are juxtaposed with a space therebetween in the longitudinal direction (x1 direction) in the sheet-like article 1 forming the absorbent core 24. From the viewpoint of providing intermediate lateral joined regions 43, 43 (described further below) between adjacent unit portions 40, it is preferable that the respective spaces between the front unit portion 40A, the crotch unit portion 40C, and the rear unit portion 40B in the longitudinal direction (x1 direction) are uniform. In the diaper 10, the front unit portion 40A, the crotch unit portion 40C, and the rear unit portion 40B are spaced uniformly in the longitudinal direction (x1 direction) in the sheet-like article 1.

In the diaper 10, as illustrated in FIG. 2, in each of the front unit portion 40A, the crotch unit portion 40C, and the rear unit portion 40B arranged in the sheet-like article 1 forming the absorbent core 24, the absorbent units 4 are arranged such that their longitudinal direction (x1 direction) is oriented in the diaper 10's article longitudinal direction X. Preferably, in the diaper 10, each of the front unit portion 40A, the crotch unit portion 40C, and the rear unit portion 40B is formed by arranging a plurality of absorbent units 4 in the lateral direction (y1 direction), which are arranged such that the absorbent unit 4's longitudinal direction (x1 direction) is oriented in the diaper 10's article longitudinal direction X. More preferably, the plurality of absorbent units 4 are arranged parallel to the diaper 10's article longitudinal direction X such that the absorbent units 4 do not intersect with one another. Each of the front unit portion 40A, the crotch unit portion 40C, and the rear unit portion 40B in the sheet-like article 1 illustrated in FIG. 3 is formed by using a plurality of the absorbent units 4 respectively including long base portions 2 with a uniform width, and by arranging the absorbent units 4 side by side in the lateral direction (y1 direction) and parallel to the longitudinal direction (x1 direction) of the sheet-like article 1 such that the longitudinal direction (x1 direction) of the absorbent units 4 is oriented along the article longitudinal direction X of the diaper 10. In each of the front unit portion 40A, the crotch unit portion 40C, and the rear unit portion 40B, from the viewpoint of facilitating movement of the absorbent units 4, there is no intervening member present between the absorbent units 4, 4 adjacent to one another in the lateral direction (y1 direction) of the long base portions 2 (absorbent units 4). Stated differently, the absorbent unit 4 in the unit portions 40 is not wrapped by an intervening member.

As illustrated in FIGS. 3 and 4, in a state before use, the front unit portion 40A, the crotch unit portion 40C, and the rear unit portion 40B arranged in the sheet-like article 1 forming the absorbent core 24 form an absorbent region AT in which the plurality of absorbent units 4, each oriented in the longitudinal direction (x1 direction), are arranged in the lateral direction (y1 direction). In the diaper 10, the absorbent region AT refers to a region combining the front unit portion 40A, the crotch unit portion 40C, and the rear unit portion 40B. From the viewpoint of facilitating absorption of liquid by the regions in which the water-absorbent polymer particles 3 are fixed, in a planar view of the sheet-like article 1 in a state before use, the percentage of the absorbent region AT to the entire sheet-like article 1 is preferably 20% or greater, more preferably 50% or greater, and preferably 95% or less, more preferably 90% or less, and more specifically, preferably from 20 to 95%, more preferably from 50 to 90%.

Note that, in a planar view of the sheet-like article 1, regions other than the absorbent region AT—i.e., preferably, regions other than the front unit portion 40A, the crotch unit portion 40C, and the rear unit portion 40B—constitute non-slit regions NT described further below.

It is preferable that preferably 2 pieces or more, more preferably 10 pieces or more, and preferably 1000 pieces or fewer, more preferably 500 pieces or fewer, and more specifically, preferably from 2 to 1000 pieces, more preferably from 10 to 500 pieces, of the absorbent units 4 are arranged in each of the front unit portion 40A, the crotch unit portion 40C, and the rear unit portion 40B.

In the diaper 10, as illustrated in FIGS. 3 and 4, the sheet-like article 1 forming the absorbent core 24 includes a single base sheet 2b, and non-slit regions NT are provided in: both lateral sides, along the longitudinal direction (x1 direction), of the base sheet 2*b*; both end portions thereof in the longitudinal direction (x1 direction); and locations between both end portions in the longitudinal direction (x1 direction). The plurality of long base portions 2 formed by a later-described cutting step are provided between these non-slit regions NT. Preferably, in the diaper 10, the non-slit regions NT in the sheet-like article 1 include: a pair of longitudinal non-slit regions NT1, NT1 extending in the longitudinal direction (x1 direction) at the respective lateral sides which are along the longitudinal direction (x1 direction); a pair of lateral non-slit regions NT2, NT2 extending in the lateral direction (y1 direction) at the respective end portions in the longitudinal direction (x1 direction); and two intermediate lateral non-slit regions NT3, NT3 extending in the lateral direction (y1 direction), each being provided between the unit portions 40 adjacent to one another in the longitudinal direction (x1 direction). Providing these non-slit regions NT (the pair of longitudinal non-slit regions NT1, NT1, the pair of lateral non-slit regions NT2, NT2, and the two intermediate lateral non-slit regions NT3, NT3) is advantageous in that the sheet form of the sheet-like article 1 is easy to maintain and the structure is less prone to getting disarranged, and the sheet is easy to transport during manufacture.

In the diaper 10, as illustrated in FIGS. 3 and 4, the sheet-like article 1, which is the absorbent core 24, includes: a pair of longitudinal joined regions 41, 41 extending in the longitudinal direction (x1 direction) at respective lateral sides which are along the longitudinal direction (x1 direction); a pair of lateral joined regions 42, 42 extending in the lateral direction (y1 direction) at respective end portions in the longitudinal direction (x1 direction); and intermediate lateral joined regions 43, 43 extending in the lateral direction (y1 direction) between the lateral joined regions 42, 42. The sheet-like article 1 is joined at the longitudinal joined regions 41, 41, the lateral joined regions 42, 42, and the intermediate lateral joined regions 43, 43 to a constituent member that constitutes the diaper 10 and that is adjacent on at least either an upper side or a lower side in the thickness direction, and each of the unit portions includes a section in which neither the upper side nor the lower side thereof in the thickness direction is joined to the constituent member. Stated differently, the sheet-like article 1 is in a state not joined to the constituent member above and below the unit portions.

Preferably, the pair of longitudinal joined regions 41, 41 is joined and fixed by a known joining means (such as an adhesive or fusion-bonding). In the diaper 10, as illustrated in FIG. 4, joining is achieved by applying a hot-melt adhesive HM extending in the longitudinal direction (x1 direction) to the pair of longitudinal non-slit regions NT1, NT1. In the diaper 10, the pair of longitudinal joined regions 41, 41 only needs to be provided in the pair of longitudinal non-slit regions NT1, NT1 on one face (skin-facing surface) of the sheet-like article 1 (absorbent core 24). In the sheet-like article 1 illustrated in FIG. 5, however, from the viewpoint of improving joining stability between the sheet-like article 1 and the constituent member of the diaper 10, the longitudinal joined regions are arranged not only in the pair of longitudinal non-slit regions NT1, NT1 on the one face (skin-facing surface) but also on the other face (non-skin-facing surface). In each of the longitudinal joined regions 41 on the one face and the other face, the hot-melt adhesive HM is applied along the respective longitudinal non-slit regions NT1. The hot-melt adhesive HM is applied substantially parallel to the longitudinal direction (x1 direction). The hot-melt adhesive HM applied to each of the longitudinal non-slit regions NT1 is arranged in a manner extending between both end portions, in the longitudinal direction (x1 direction), in each of the longitudinal non-slit regions NT1.

In the diaper 10, as illustrated in FIG. 4, the longitudinal joined regions 41 extend continuously in the longitudinal direction (x1 direction) in the sheet-like article 1's respective lateral sides which are along the longitudinal direction (x1 direction). In the diaper 10, the longitudinal joined regions 41 are formed so as to extend continuously in the longitudinal direction (x1 direction) by applying the hot-melt adhesive HM continuously in the longitudinal direction (x1 direction) along the respective longitudinal non-slit regions NT1 on the one face and the other face of the sheet-like article 1. By forming the longitudinal joined regions 41 so as to extend continuously in the longitudinal direction (x1 direction), the joining strength between the sheet-like article 1 and the diaper 10's constituent member can be improved. Note, however, that in the diaper 10, the longitudinal joined regions 41 may be formed by applying the hot-melt adhesive HM to the respective longitudinal non-slit regions NT1 intermittently with spaces therebetween in the longitudinal direction (x1 direction).

Further, in the diaper 10, as illustrated in FIG. 3, the longitudinal non-slit regions NT1 on the one face and the other face respectively have non-application portions 44, 44, in each of which no hot-melt adhesive HM is applied, formed at respective lateral-side outer edges along the longitudinal direction (x1 direction). Preferably, each non-application portion 44 is arranged along the respective longitudinal joined region 41 on the outermost side, in the lateral direction (y1 direction), of the longitudinal joined region 41. Further, each non-application portion 44 is arranged substantially parallel to the respective longitudinal joined region 41. Providing non-application portions 44, 44 at the respective lateral side edges, along the longitudinal direction (x1 direction), of the sheet-like article 1 serving as the absorbent core 24 improves texture in sections in contact with the wearer's legs when the user wearing the diaper 10 moves his/her legs.

In the diaper 10, as illustrated in FIG. 4, the length (referred to also as "width W1"), in the lateral direction (y1 direction), of the longitudinal joined region 41 is greater than or equal to the length (referred to also as "width W"), in the lateral direction (y1 direction), of the long base portion 2 (see FIG. 5). In the diaper 10, the width W1 of each longitudinal joined region 41 is formed longer than the width W of a single piece of the long base portions 2 constituting the unit portions 40 (the front unit portion 40A, the crotch unit portion 40C, and the rear unit portion 40B). By making the width W1 of the longitudinal joined region 41 equal to or longer than the width W of a single long base portion 2, it is possible to suppress disarrangement in the structure of the absorbent core 24, and at the same time, improve softness and leakage preventability.

As regards the ratio of the width W1 of each longitudinal joined region 41 to the width W of a single long base portion 2, in the diaper 10, as illustrated in FIG. 4, from the viewpoint of suppressing disarrangement of the structure of the absorbent core 24 and, at the same time, improving softness and leakage preventability, it is preferable that the width W1 of each longitudinal joined region 41 is preferably 2 times or greater, more preferably 3 times or greater, and preferably 100 times or less, more preferably 10 times or less, and more specifically, preferably from 2 to 100 times, more preferably from 3 to 10 times, the width W of a single long base portion 2.

More specifically, from the same viewpoint, the width W1 of each longitudinal joined region 41 is preferably 3 mm or greater, more preferably 5 mm or greater, and preferably 50 mm or less, more preferably 10 mm or less, and more specifically, preferably from 3 to 50 mm, more preferably from 5 to 10 mm.

Further, from the same viewpoint, the width W of a single long base portion 2 is preferably 0.3 mm or greater, more preferably 0.6 mm or greater, and preferably 10 mm or less, more preferably 2 mm or less, and more specifically, preferably from 0.3 to 10 mm, more preferably from 0.6 to 2 mm. The width (WO) of the absorbent core 24 (sheet-like article 1) is from 50 to 300 mm.

It is preferable that the pair of lateral joined regions 42, 42 is joined by an adhesive. In the diaper 10, as illustrated in FIG. 4, joining is achieved by applying a hot-melt adhesive HM extending in the lateral direction (y1 direction) to the pair of lateral non-slit regions NT2, NT2. In the diaper 10, the pair of lateral joined regions 42, 42 only needs to be provided in the pair of lateral non-slit regions NT2, NT2 on one face (skin-facing surface) of the sheet-like article 1 (absorbent core 24). In the sheet-like article 1 illustrated in FIG. 5, however, from the viewpoint of improving joining stability between the sheet-like article 1 and the constituent member of the diaper 10, the lateral joined regions are arranged not only in the pair of lateral non-slit regions NT2, NT2 on the one face (skin-facing surface) but also on the other face (non-skin-facing surface). In each of the lateral joined regions 42 on the one face and the other face, the hot-melt adhesive HM is applied in the lateral direction (y1 direction) along the respective lateral non-slit region NT2. The hot-melt adhesive HM is applied substantially parallel to the lateral direction (y1 direction) to each of the lateral non-slit regions NT2. The hot-melt adhesive HM applied to each of the lateral non-slit regions NT2 is arranged within each of the lateral non-slit regions NT2 in a manner extending between the pair of longitudinal joined regions 41, 41. Stated differently, the hot-melt adhesive HM in each of the lateral joined regions 42 on the one face and the other face is connected at both end portions, in the lateral direction (y1 direction), to the hot-melt adhesive HM in the respective longitudinal joined regions 41, 41.

As illustrated in FIG. 4, in each of the lateral joined regions 42 on the one face and the other face of the sheet-like article 1, the hot-melt adhesive HM is applied intermittently with spaces therebetween in the lateral direction (y1 direction) in each of the lateral non-slit regions NT2 located at the respective end portions, in the longitudinal direction (x1 direction), of the sheet-like article 1. In the diaper 10, the lateral joined regions 42 are formed in an extending manner by applying the hot-melt adhesive HM with spaces therebetween in the lateral direction (y1 direction) along the respective lateral non-slit regions NT2. Note, however, that, in the diaper 10, the hot-melt adhesive HM may be applied continuously in the lateral direction (y1 direction) in the respective lateral non-slit regions NT2.

In the diaper 10, as illustrated in FIG. 4, the length (referred to also as "width W2"), in the longitudinal direction (x1 direction), of the lateral joined region 42 is longer than the length (referred to also as "width W3"), in the longitudinal direction (x1 direction), of a later-described intermediate lateral joined region 43. By making the width W2 of the lateral joined region 42 longer than the width W3 of the intermediate lateral joined region 43, it is possible to suppress disarrangement of the structure of the absorbent core 24, and at the same time, improve softness and leakage preventability.

In the diaper 10, as illustrated in FIG. 4, from the viewpoint of suppressing disarrangement of the structure of the absorbent core 24 and, at the same time, improving softness and leakage preventability, it is preferable that the ratio of the width W2 of each lateral joined region 42 is preferably 1.2 times or greater, more preferably 1.5 times or greater, and preferably 10 times or less, more preferably 5 times or less, and more specifically, preferably from 1.2 to 10 times, more preferably from 1.5 to 5 times, the width W3 of each intermediate lateral joined region 43.

More specifically, from the same viewpoint, the width W2 of each lateral joined region 42 is preferably 5 mm or greater, more preferably 10 mm or greater, and preferably 100 mm or less, more preferably 30 mm or less, and more specifically, preferably from 5 to 100 mm, more preferably from 10 to 30 mm.

Further, from the same viewpoint, the width W3 of each intermediate lateral joined region 43 is preferably 3 mm or greater, more preferably 5 mm or greater, and preferably 50 mm or less, more preferably 20 mm or less, and more specifically, preferably from 3 to 50 mm, more preferably from 5 to 20 mm.

It is preferable that the two intermediate lateral joined regions 43, 43 are joined by an adhesive. In the diaper 10, as illustrated in FIG. 4, joining is achieved by applying a hot-melt adhesive HM extending in the lateral direction (y1 direction) to the two intermediate lateral non-slit regions NT3, NT3. In the diaper 10, the intermediate lateral joined regions 43 are joined between the unit portions 40 that are adjacent to one another in the longitudinal direction (x1 direction). By achieving joining of the intermediate lateral joined regions 43 at locations between the unit portions 40 that are adjacent to one another in the longitudinal direction (x1 direction), it is possible to suppress the absorbent units 4 of the unit portions 40 from gathering toward the center in the article lateral direction Y when the diaper 10 is worn. In the diaper 10, the intermediate lateral joined regions 43, 43 only need to be provided in the intermediate lateral non-slit regions NT3, NT3 on one face (skin-facing surface) of the sheet-like article 1 (absorbent core 24). In the sheet-like article 1 illustrated in FIG. 5, however, from the viewpoint of improving joining stability between the sheet-like article 1 and the constituent member of the diaper 10, the intermediate lateral joined regions are arranged not only in the intermediate lateral non-slit regions NT3, NT3 on the one face (skin-facing surface) but also on the other face (non-skin-facing surface). In each of the intermediate lateral joined regions 43 on the one face and the other face, the hot-melt adhesive HM is applied in the lateral direction (y1 direction) along the respective intermediate lateral non-slit region NT3. The hot-melt adhesive HM is applied substantially parallel to the lateral direction (y1 direction). The hot-melt adhesive HM applied to each of the intermediate lateral non-slit regions NT3 is arranged within each of the intermediate lateral non-slit regions NT3 in a manner extending between the pair of longitudinal joined regions 41, 41. Stated differently, the hot-melt adhesive HM in each of the intermediate lateral joined regions 43 on the one face and the other face is connected at both end portions, in the lateral direction (y1 direction), to the hot-melt adhesive HM in the respective longitudinal joined regions 41, 41.

As illustrated in FIG. 4, in each of the intermediate lateral joined regions 43 on the one face and the other face of the sheet-like article 1, the hot-melt adhesive HM is applied, at a location between the pair of lateral joined regions 42, 42 separated in the longitudinal direction (x1 direction), intermittently with spaces therebetween in the lateral direction (y1 direction). In the diaper 10, each of the intermediate lateral joined regions 43 is formed in an extending manner by applying the hot-melt adhesive HM with spaces therebetween in the lateral direction (y1 direction) along the respective intermediate lateral non-slit regions NT3. Further, the positions where the hot-melt adhesive HM is applied intermittently in the lateral direction (y1 direction) in each of the intermediate lateral joined regions 43 respectively match, in the longitudinal direction (x1 direction), the positions where the hot-melt adhesive HM is applied intermittently in the lateral direction (y1 direction) in each of the lateral joined regions 42; and the sections where the hot-melt adhesive HM is arranged in each intermediate lateral joined region 43 are located respectively collinear, in the longitudinal direction (x1 direction), with the sections where the hot-melt adhesive HM is arranged in each lateral joined region 42. Note, however, that in the diaper 10, the hot-melt adhesive HM may be applied continuously in the lateral direction (y1 direction) in the respective intermediate lateral non-slit regions NT3.

In the diaper 10, as illustrated in FIG. 4, the water-absorbent polymer particles 3 are not arranged in the longitudinal joined regions 41, 41, the lateral joined regions 42, 42, and the intermediate lateral joined regions 43, 43. By not providing the water-absorbent polymer particles 3 to the pair of longitudinal joined regions 41, 41, the pair of lateral joined regions 42, 42, and the intermediate lateral joined regions 43, 43, it is possible to achieve, for example, the effects of stably achieving joinability in the pair of longitudinal joined regions 41, 41, the pair of lateral joined regions 42, 42, and the intermediate lateral joined regions 43, 43 even when the absorbent core 24 has absorbed body fluid, and easily maintaining the sheet shape of the sheet-like article 1 even in a swollen state. Note that the expression "the water-absorbent polymer particles 3 are not arranged" encompasses cases where absolutely no water-absorbent polymer particle 3 is arranged, and also cases where water-absorbent polymer particles 3 are arranged in an amount that achieves the aforementioned effects.

Figure 7:
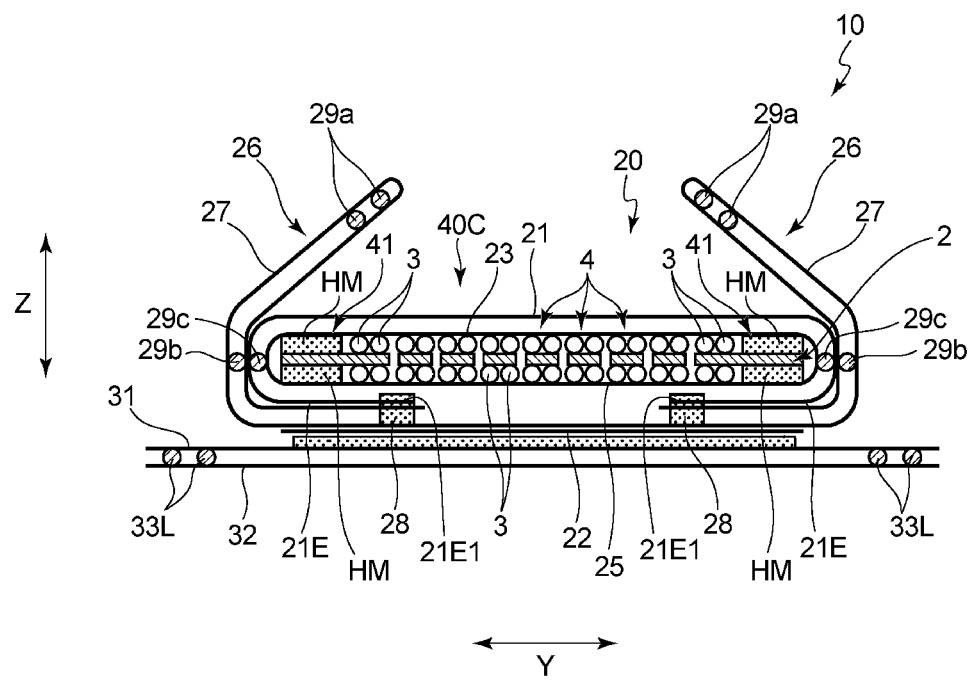
FIG. 7 is a cross-sectional view taken along line VII-VII in the diaper illustrated in FIG. 2.
Figure 8:
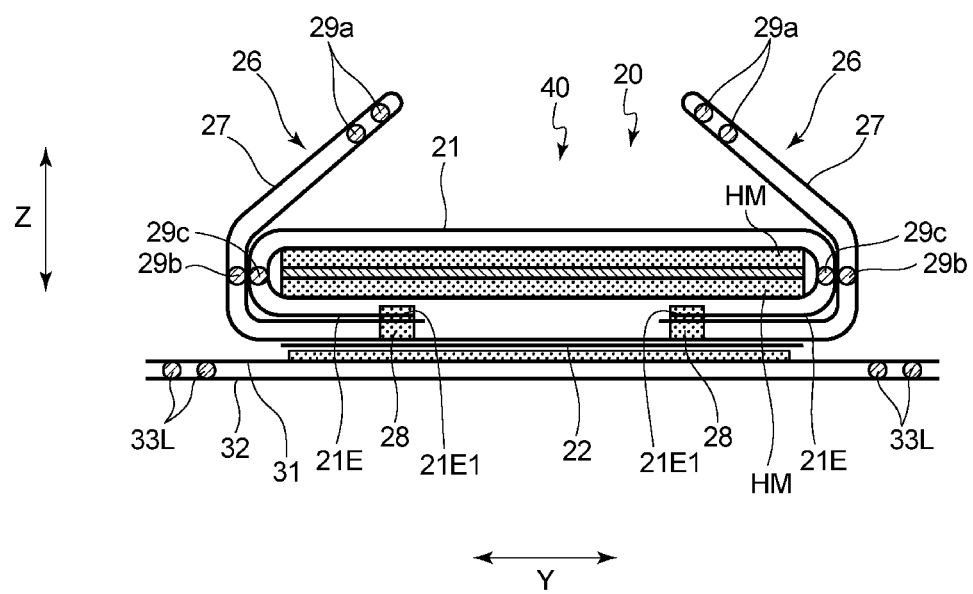
FIG. 8 is a cross-sectional view taken along line VIII-VIII in the diaper illustrated in FIG. 2.

In the diaper 10, as illustrated in FIGS. 7 and 8, the sheet-like article 1 is joined by the hot-melt adhesive HM at the pair of longitudinal joined regions 41, 41, the pair of lateral joined regions 42, 42, and the intermediate lateral joined regions 43, 43 to a constituent member that constitutes the diaper 10 and that is adjacent on at least either an upper side or a lower side in the thickness direction Z. A sheet-like member-such as the topsheet 21, the backsheet 22, or the core-wrap sheet 25—is an example of the constituent member that constitutes the diaper 10 and is adjacent on at least either an upper side or a lower side in the diaper 10's thickness direction Z and to which the pair of longitudinal joined regions 41, 41, the pair of lateral joined regions 42, 42, and the intermediate lateral joined regions 43, 43 of the sheet-like article 1, which forms the absorbent core 24, are joined. In the diaper 10, the core-wrap sheet 25 covers the sheet-like article 1 (absorbent core 24), and the sheet-like article 1 (absorbent core 24) is joined at the pair of longitudinal joined regions 41, 41, the pair of lateral joined regions 42, 42, and the intermediate lateral joined regions 43, 43; thus, the core-wrap sheet 25 serves as the aforementioned constituent member. In the diaper 10, both the upper and lower sides, in the thickness direction (z1 direction), of the sheet-like article 1 (absorbent core 24) are joined to the core-wrap sheet 25 at the pair of longitudinal joined regions 41, 41, the pair of lateral joined regions 42, 42, and the intermediate lateral joined regions 43, 43. By joining both the upper and lower sides, in the thickness direction (z1 direction), of the sheet-like article 1 (absorbent core 24) to the core-wrap sheet 25 at the pair of longitudinal joined regions 41, 41, the pair of lateral joined regions 42, 42, and the intermediate lateral joined regions 43, 43, the sheet shape of the sheet-like article 1 (absorbent core 24) is easy to retain, and the structure is less prone to getting disarranged. Further, in the diaper 10, the upper and lower sides, in the thickness direction (z1 direction), of the sheet-like article 1 are not joined to the core-wrap sheet 25 in the front unit portion 40A, the crotch unit portion 40C, and the rear unit portion 40B, which constitute the absorbent region AT. Thus, softness in the front unit portion 40A, the crotch unit portion 40C, and the rear unit portion 40B, which constitute the absorbent region AT, is improved, making it less likely to give the wearer an uncomfortable feel. In the diaper 10, it is only necessary that each of the front unit portion 40A, the crotch unit portion 40C, and the rear unit portion 40B—which constitute the absorbent region AT—includes a section in which neither the upper side nor the lower side, in the thickness direction (z1 direction), of the sheet-like article 1 is joined to the core-wrap sheet 25, but it is preferable that the entire region of each of the front unit portion 40A, the crotch unit portion 40C, and the rear unit portion 40B is not joined to the core-wrap sheet. Stated differently, it is preferable that joining is not performed in regions other than the aforementioned joined regions.

In the diaper 10, as illustrated in FIGS. 7 and 8, the core-wrap sheet 25 joined to the absorbent core 24 at the longitudinal joined regions 41, 41, the lateral joined regions 42, 42, and the intermediate lateral joined regions 43, 43 is joined to another constituent member constituting the diaper 10. In the diaper 10, the other constituent member constituting the diaper 10 is the outer cover 30, and the core-wrap sheet 25 is joined to the outer cover 30 by means of joined regions 28 (described later). By joining the core-wrap sheet 25—which is joined to the absorbent core 24 at the pair of longitudinal joined regions 41, 41, the pair of lateral joined regions 42, 42, and the intermediate lateral joined regions 43, 43—to the outer cover 30, even when the absorbent core 24 is compressed inwardly in the width direction by, for example, the opening/closing movement of the wearer's legs while the diaper 10 is worn, the absorbent core can return to the outward side, in the article lateral direction Y, by moving together with the outer cover 30.

The outer cover 30 includes an inner sheet 31 and an outer sheet 32, and the leg elastic members 33L, which are elastic members that contract around the wearer's legs, are arranged between the inner sheet 31 and the outer sheet 32. By arranging the leg elastic members 33L in the outer cover 30 to which the core-wrap sheet 25 is joined, the outer cover's fittability to the wearer's legs is improved, and the absorbent core 24's restorability in the width direction can be further improved.

In the diaper 10, as illustrated in FIG. 3, from the viewpoint of reducing uncomfortable feel by improving bendability (softness) of the crotch portion, it is preferable that the percentage of the length (L1), in the longitudinal direction (x1 direction), of each unit portion 40 (i.e., each of the front unit portion 40A, the crotch unit portion 40C, and the rear unit portion 40B) to the length (L0), in the longitudinal direction (x1 direction), of the sheet-like article 1—that is, the percentage of the length, in the longitudinal direction (x1 direction), of a single long base portion 2 constituting each unit portion 40 (the front unit portion 40A, the crotch unit portion 40C, and the rear unit portion 40B) to the length (L0), in the longitudinal direction (x1 direction), of the sheet-like article 1—is preferably 5% or greater, more preferably 10% or greater, and preferably 49% or less, more preferably 40% or less, and more specifically, preferably from 5 to 49%, more preferably from 10 to 40%.

In the diaper 10, as illustrated in FIG. 3, from the same viewpoint, it is preferable that the length (L1), in the longitudinal direction (x1 direction), of each of the front unit portion 40A, the crotch unit portion 40C, and the rear unit portion 40B (i.e., each long base portion 2) is preferably 20 mm or greater, more preferably 50 mm or greater, and preferably 495 mm or less, more preferably 485 mm or less, and more specifically, preferably from 20 to 495 mm, more preferably from 50 to 485 mm. The length (LO) of the absorbent core 24 (sheet-like article 1) is around 100 to 1000 mm.

Further, in the diaper 10, as illustrated in FIG. 4, from the same viewpoint, it is preferable that the percentage of the width (W) (the length in the lateral direction (y1 direction)) of each long base portion 2 to the width (W0) of the sheet-like article 1 is preferably 0.1% or greater, more preferably 0.2% or greater, and preferably 20% or less, more preferably 4% or less, and more specifically, preferably from 0.1 to 20%, more preferably from 0.2 to 4%.

In the diaper 10, the long base portions 2 constituting the absorbent units 4 in each of the front unit portion 40A, the crotch unit portion 40C, and the rear unit portion 40B are preferably made of a hydrophilic sheet from the viewpoint of easy diffusibility of liquid in the absorbent region AT and improvement in usage efficiency of the water-absorbent polymer 3. Examples of hydrophilic sheets include paper, nonwoven fabrics, cloths, and synthetic sponge made by foaming synthetic resins, and among the above, nonwoven fabrics are preferably used, from the viewpoint of relatively high tensile strength despite its thinness and capability of achieving softness and thinness. Examples of preferably usable nonwoven fabrics include hydrophilic nonwoven fabrics including hydrophilic fibers as constituent fibers, and hydrophilic nonwoven fabrics including, as constituent fibers, fibers obtained by imparting hydrophilicity to synthetic fibers. The basis weight of the nonwoven fabric is preferably from 5 to 100 g/m$^2$, more preferably from 10 to 40 g/m$^2$.

In the diaper 10, various types of polymers conventionally used in the technical field of absorbent articles can be used for the water-absorbent polymer 3 to be fixed to the surface of the one face and the other face of the long base portions 2. Examples include sodium polyacrylate, (acrylic acid-vinyl alcohol) copolymer, crosslinked sodium polyacrylate, (starch-acrylic acid) graft polymer, (isobutylene-maleic anhydride) copolymer and saponified products thereof, potassium polyacrylate, and cesium polyacrylate. One type of polymer may be used singly, or two or more types may be used as a mixture. Based on differences in their shape, there are various types of water-absorbent polymer particles 3, such as the amorphous type, block type, barrel type, pellet-agglomeration type, and spherical type; any type of particle may be used. In the sheet-like article 1, spherical-type particles are used.

Examples of methods for fixing the water-absorbent polymer particles 3 to the one face and the other face of the long base portions 2 include methods using adhesives and chemical fixing methods employing a hydrogen bond etc., and in cases where the long base portions 2 are a nonwoven fabric or a cloth, the constituent fibers may be napped, and the water-absorbent polymer particles may be fixed among the napped constituent fibers. In the sheet-like article 1 illustrated in FIGS. 5 and 6, a hot-melt adhesive HM is employed. More specifically, the water-absorbent polymer particles 3 of the sheet-like article 1 are fixed to the one face and the other face of the long base portions 2 by means of the hot-melt adhesive HM. Fixing the water-absorbent polymer particles 3 to the surface of the long base portions 2 by means of the hot-melt adhesive HM suppresses the water-absorbent polymer particles 3 from falling off in a state before use of the sheet-like article 1 and in a state after the polymer has swollen.

Examples of the hot-melt adhesive HM include styrene-based and olefin-based adhesives. Examples of styrene-based hot-melt adhesives that may be used include styrene-butadiene-styrene (SBS) copolymers, styrene-isoprene-styrene (SIS) copolymers, styrene-ethylene-butylene-styrene (SEBS) copolymers which are hydrogenated products of SBS, and blended hot-melt adhesives in which two or more types of the above are blended. Among the above, particularly, a blended hot-melt adhesive including SIS and SBS or a blended hot-melt adhesive including SIS and SEBS is preferably used from the viewpoint of the ease of balancing tack force and cohesive force. The amount of hot-melt adhesive applied is preferably from 0.5 to 100 g/m$^2$, more preferably from 5 to 50 g/m$^2$.

In the sheet-like article 1, the water-absorbent polymer particles 3 only need to be fixed only to the surface of one face (e.g., the skin-facing surface) of the respective long base portions 2, but in the sheet-like article 1 illustrated in FIG. 5, from the viewpoint of improving the liquid absorption performance of the sheet-like article 1, the water-absorbent polymer particles are also fixed to the surface of the other face (e.g., the non-skin-facing surface) of the respective long base portions 2, in addition to the surface of the one face (e.g., the skin-facing surface) thereof. Herein, it is preferable that the type of polymer is the same among the water-absorbent polymer particles 3 arranged on the surface of the one face (e.g., the skin-facing surface) of the front unit portion 40A, the crotch unit portion 40C, and the rear unit portion 40B. Similarly, it is preferable that the type of polymer is the same among the water-absorbent polymer particles 3 arranged on the surface of the other face (e.g., the non-skin-facing surface) of the front unit portion 40A, the crotch unit portion 40C, and the rear unit portion 40B. The following describes, as an example, the water-absorbent polymer particles 3 arranged on the surface of one face (e.g., the skin-facing surface) and the water-absorbent polymer particles 3 arranged on the surface of the other face (e.g., the non-skin-facing surface) of the front unit portion 40A, the crotch unit portion 40C, and the rear unit portion 40B.

In cases of fixing the water-absorbent polymer particles 3 to the surface of both faces (the skin-facing surface and the non-skin-facing surface) of the respective long base portions 2, from the viewpoint of further achieving the aforementioned effects, it is preferable that the basis weight of the water-absorbent polymer 3 fixed on the surface of the other face (e.g., the non-skin-facing surface) of the long base portions 2 is greater than the basis weight of the water-absorbent polymer 3 fixed on the surface of the one face (e.g., the skin-facing surface) of the long base portions 2. The basis weight of the water-absorbent polymer 3 fixed on the surface of the one face (e.g., the skin-facing surface) of the long base portions 2 is preferably from 10 to 250 g/m$^2$, more preferably from 30 to 150 g/m$^2$. The basis weight of the water-absorbent polymer 3 fixed on the surface of the other face (e.g., the non-skin-facing surface) of the long base portions 2 is preferably from 30 to 400 g/m$^2$, more preferably from 50 to 300 g/m$^2$.

The basis weight of the water-absorbent polymer 3 fixed on the one face (the skin-facing surface) side of the long base portions 2 and the basis weight of the water-absorbent polymer 3 fixed on the other face (the non-skin-facing surface) side of the long base portions 2 are measured according to the following method.

{Method for Measuring Basis Weight of Water-Absorbent Polymer 3 Fixed on One Face (Skin-Facing Surface) Side of Long Base Portions 2 and Basis Weight of Water-Absorbent Polymer 3 Fixed on Other Face (Non-Skin-Facing Surface) Side of Long Base Portions 2}

To prevent the water-absorbent polymer fixed on the non-skin-facing surface side of the long base portions 2 from falling off, the water-absorbent polymer is re-fixed from the upper surface thereof with an adhesive for example. Then, the water-absorbent polymer fixed on the skin-facing surface side is removed from the long base portions 2 with a solvent for example, and the adhesive adhering to the water-absorbent polymer is rinsed off. After drying the water-absorbent polymer, the weight of the water-absorbent polymer that had been fixed on the skin-facing surface side is measured. From the area of the long base portions 2 in the section where the water-absorbent polymer was fixed and the weight of the removed water-absorbent polymer, the weight of the water-absorbent polymer fixed per unit area is calculated, to find the basis weight of the water-absorbent polymer on the skin-facing surface side. The measurement is performed with five sheets, and the average value is calculated.

The basis weight of the water-absorbent polymer on the non-skin-facing surface side is found in a similar manner; the water-absorbent polymer on the skin-facing surface side is fixed, the water-absorbent polymer on the non-skin-facing surface side is removed and rinsed, and the basis weight is calculated.

In cases of fixing the water-absorbent polymer particles 3 to the surface of both faces (the skin-facing surface and the non-skin-facing surface) of the respective long base portions 2, from the viewpoint of causing the surface of the non-skin-facing surface, which is farther from the wearer's skin, to retain a large amount of liquid and improving texture to the touch by preventing liquid from remaining on the surface of the skin-facing surface, it is preferable that the water-absorbent polymer 3 fixed on the surface of the one face (the skin-facing surface) of the long base portions 2 has a higher liquid permeation performance under pressure and a smaller centrifugal retention amount than the water-absorbent polymer 3 fixed on the surface of the other face (the non-skin-facing surface) of the long base portions 2. As described herein, it is preferable that the type of the water-absorbent polymer 3 fixed on the surface of the one face (the skin-facing surface) of the long base portions 2 is different from the type of the water-absorbent polymer 3 fixed on the surface of the other face (the non-skin-facing surface) of the long base portions 2. Herein, "the type of the water-absorbent polymer is different" means that the liquid permeation rate under pressure or the centrifugal retention amount is different. From the above viewpoint, as for the water-absorbent polymer 3 fixed on the surface of the one face (the skin-facing surface) of the long base portions 2, the liquid permeation rate under a pressure of 2.0 kPa is preferably 20 ml/minute or greater, more preferably 40 ml/minute or greater, and preferably 1000 ml/minute or less, more preferably 800 ml/minute or less, and more specifically, preferably from 20 to 1000 ml/minute, more preferably from 40 to 800 ml/minute. As for the water-absorbent polymer particles 3 fixed on the surface of the other face (the non-skin-facing surface) of the long base portions 2, the liquid permeation rate under a pressure of 2.0 kPa is preferably 0 ml/minute or greater, more preferably 10 ml/minute or greater, and preferably 400 ml/minute or less, more preferably 200 ml/minute or less, and more specifically, preferably from 0 to 400 ml/minute, more preferably from 10 to 200 ml/minute. The liquid permeation rate under pressure is found according to the following measurement method.

{Method for Measuring Liquid Permeation Rate Under Pressure}

The liquid permeation rate under pressure is measured by employing the measurement method and measurement device disclosed in JP 2003-235889 A. In a 100-ml glass beaker, 0.32±0.005 g of the water-absorbent polymer, which is the sample to be measured, is immersed in a sufficient amount of physiological saline solution (0.9 mass % sodium chloride aqueous solution) sufficient for swelling the water-absorbent polymer—e.g., a physiological saline solution in an amount equal to or more than 5 times the saturation absorption amount of the water-absorbent polymer—and the sample is left for 30 minutes. Provided separately is a filter cylindrical tube in which a metal mesh (mesh opening: 150 μm; bio-column sintered stainless steel filter 30SUS sold by Sansyo Co., Ltd.) and a fine tube (inner diameter: 4 mm; length: 8 cm) with a valve (inner diameter: 2 mm) are provided to the lower end of an opening in a vertically-arranged cylinder (inner diameter: 25.4 mm). In a state where the valve is closed, the whole content of the aforementioned beaker, including the swollen measurement sample, is poured into the cylindrical tube. Then, a 2-mm-dia. circular cylindrical rod having, at its tip end, a metal mesh with a mesh opening of 150 μm and a diameter of 25 mm is inserted into the filter cylindrical tube so that the metal mesh comes into contact with the measurement sample, and further, a weight is placed on the measurement sample such that a load of 2.0 kPa is applied thereto. The sample is left in this state for 1 minute, the valve is opened to let the liquid pass through, and the time (T1) (seconds) from when the liquid level inside the filter cylindrical tube is at the 60 ml scale line to when the liquid level reaches the 40 ml scale line (i.e., the time required for 20 ml of liquid to pass through) is measured. By using the measured time T1 (seconds), the liquid permeation rate under a pressure of 2.0 kPa is calculated from the equation below. In the equation, T0 (seconds) is a measurement value of the time required for 20 ml of physiological saline solution to pass through the metal mesh when no measurement sample is placed inside the filter cylindrical tube.

$$\text{Liquid permeation rate under pressure (ml/min)}=20\times 60/(T1-T0)$$

The measurement is performed five times (n=5); the highest and lowest values are eliminated, and the average value of the remaining three samples is found as the measurement value. The measurement is performed at 23±2° C. at a humidity of 50±5%, and the sample is stored in this environment for 24 hours or longer before measurement. The method for measuring the liquid permeation rate under pressure is described in further detail in paragraphs {0008} and {0009} of JP 2003-235889 A, and the measurement device is illustrated in FIGS. 1 and 2 of the same publication.

From the aforementioned viewpoint, as for the water-absorbent polymer 3 fixed on the surface of the one face (the skin-facing surface) of the long base portions 2, the centrifugal retention amount (water absorption amount) is preferably 20 g/g or greater, more preferably 25 g/g or greater, and preferably 50 g/g or less, more preferably 45 g/g or less, and more specifically, preferably from 20 to 50 g/g, more preferably from 25 to 45 g/g. As for the water-absorbent polymer 3 fixed on the surface of the other face (the non-skin-facing surface) of the long base portions 2, the centrifugal retention amount (water absorption amount) is preferably 25 g/g or greater, more preferably 30 g/g or greater, and preferably 65 g/g or less, more preferably 55 g/g or less, and more specifically, preferably from 25 to 65 g/g, more preferably from 30 to 55 g/g. The centrifugal retention amount (water absorption amount) is found according to the following measurement method.

{Method for Measuring Centrifugal Retention Amount (Water Absorption Amount)}

The centrifugal retention amount (water absorption amount) is measured in compliance with JIS K 7223 (1996). A nylon woven fabric (sold by Sanriki Seisakusho; product name: nylon mesh; specification: 250 mesh) is cut into a rectangle that is 10 cm wide and 40 cm long, the rectangle is folded into two at the longitudinal center, and both ends are heat-sealed, to prepare a nylon bag that is 10 cm wide (inner dimension: 9 cm) and 20 cm long. Next, 1.00 g of the water-absorbent polymer, which is the sample to be measured, is weighed precisely, and is placed uniformly at the bottom of the prepared nylon bag. Then, the nylon bag containing the sample is immersed in a physiological saline solution (0.9 mass % sodium chloride aqueous solution) whose temperature has been adjusted to 25° C. After 1 hour from the start of immersion, the nylon bag is removed from the physiological saline solution, is hung in a vertical state for 1 hour to drain, and is then dehydrated by using a centrifugal drier (product of Kokusan Co., Ltd.; model: H-130C special). The dehydration is performed at 143 G (800 rpm) for 10 minutes. After dehydration, the mass of the sample is measured, and the centrifugal retention amount (water absorption amount) to be found is calculated according to the equation below.

$$\text{Centrifugal retention amount (g/g)}=(a'-b-c)/c$$

In the equation, a' is the total mass (g) of the centrifugally-dehydrated sample and the nylon bag, b is the mass (g) of the nylon bag before water absorption (when dry), and c is the mass (g) of the sample before water absorption (when dry).

The measurement is performed five times (n=5); the highest and lowest values are eliminated, and the average value of the remaining three samples is found as the measurement value. The measurement is performed at 23±2° C. at a humidity of 50±5%, and the sample is stored in this environment for 24 hours or longer before measurement.

In the sheet-like article 1 of the diaper 10, it is preferable that, in a state after swelling as illustrated in FIG. 6, the water-absorbent polymer particles 3 swell beyond the long base portion 2's lateral side edge portions 2s that extend along the longitudinal direction (x1 direction). Herein, "the water-absorbent polymer particles 3 swell beyond the long base portion 2's lateral side edge portions 2s" means, in other words, that, in a state after swelling of the sheet-like article 1, the swollen water-absorbent polymer particles 3 extend across the lateral side edge portions 2s of the long base portions 2, like the swollen water-absorbent polymer particle 3a as illustrated in FIG. 6, for example. Note that, so long as the swollen water-absorbent polymer particles 3 extend across the lateral side edge portions 2s of the long base portions 2 in a state after swelling of the sheet-like article 1, the water-absorbent polymer particles 3 may exist inward of the lateral side edge portions 2s of the long base portions 2 in a state before use of the sheet-like article 1. Alternatively, the water-absorbent polymer particles 3 may extend across the lateral side edge portions 2s of the long base portions 2 from the beginning, like the water-absorbent polymer particle 3b before use (before swelling) as illustrated in FIG. 5, for example.

Further, in the sheet-like article 1 of the diaper 10, it is preferable that, in a swollen state as illustrated in FIG. 6, the position, in the thickness direction (z1 direction), of the water-absorbent polymer particles 3 in each long base portion 2 is varied, for example vertically and/or obliquely, from the position thereof before absorbing a liquid. Herein, "in a state after swelling of the sheet-like article 1, the position, in the thickness direction (z1 direction), of each long base portion 2 is varied from the position thereof before absorbing a liquid" means that the sheet-like article is formed such that the position of each long base portion 2 in a state after swelling of the water-absorbent polymer particles 3 is varied from the position of the long base portion 2 in a state before use (before swelling) of the water-absorbent polymer particles 3.

As illustrated in FIG. 7, in the absorbent assembly 20 of the diaper 10, the topsheet 21 covers the entire surface of the skin-facing surface of the absorbent member 23 including the absorbent core 24, and includes extension portions 21E extending outward, in the article lateral direction Y, from respective lateral side edge portions of the absorbent member 23, the extension portions 21E being folded back toward the non-skin-facing surface side of the absorbent member 23 and respectively covering the absorbent member 23's non-skin-facing surface located in the respective lateral sides, along the article longitudinal direction X, of the absorbent core 24. Preferably, the absorbent assembly 20 includes the topsheet 21, which covers the skin-facing surface of the absorbent core 24, and the backsheet 22, which covers the non-skin-facing surface of the absorbent core 24. The topsheet 21 is made of a liquid-permeable sheet, and is a sheet that faces the wearer's skin when the diaper 10 is worn. The topsheet 21 covers the entire region of the skin-facing surface side, in the longitudinal direction (x1 direction), of the sheet-like article 1 forming the absorbent core 24, and the tip-end portion 21E1 of each extension portion 21E of the topsheet 21 extends beyond the respective lateral side, along the longitudinal direction (x1 direction), of the sheet-like article 1 forming the absorbent core 24, and is arranged on the non-skin-facing surface. On the non-skin-facing surface side, the backsheet 22 covers the entire region, in the longitudinal direction (x1 direction), of the sheet-like article 1 forming the absorbent core 24, and also covers the entire region in the lateral direction (y1 direction). The backsheet 22 is made of a liquid-impermeable or water-repellent sheet, and is a sheet that faces the outer cover 30.

In the diaper 10, as illustrated in FIG. 7, the tip-end portion 21E1 of each extension portion 21E of the topsheet 21 is fixed to a constituent member, of the absorbent article, adjacent on the non-skin-facing surface side. Preferably, in the diaper 10, the absorbent assembly 20 includes a pair of leak-proof cuffs 26, 26 in the respective lateral sides along the article longitudinal direction X. Each leak-proof cuff 26 is made by folding, into two, a water-repellent sheet material 27 having a rectangular shape that is long in the article longitudinal direction X, and interposing and fixing a lateral side region of the folded sheet material 27 between the backsheet 22 and the extension portion 21E of the topsheet 21. In the diaper 10, the sheet material 27 forming the leak-proof cuff 26 serves as the absorbent article's constituent member on the non-skin-facing surface side to which the tip-end portion 21E1 of the topsheet 21 is fixed. This joining forms a joined region 28 extending along the article longitudinal direction X.

In the diaper 10, the joined region 28 is formed by joining the sheet material 27 forming the leak-proof cuff 26, the tip-end portion 21E1 of the extension portion 21E of the topsheet 21, and the backsheet 22 together by using a known joining means such as heat sealing, high-frequency sealing, ultrasonic sealing, or a hot-melt adhesive. The joined region 28 may be formed as a continuous straight line, but is not limited thereto, and may be formed as an intermittent straight line having non-continuous portions in places, or may be formed as a continuous or intermittent curved line.

As illustrated in FIG. 7, in the diaper 10, the sheet material 27, in a state folded into two, has its fold line located on the inner side in the article lateral direction Y, and thread-form elastic members 29a are fixed in their stretched state inside the position of the fold line, as illustrated in FIG. 7. The contraction of the elastic members 29a causes the leak-proof cuff 26 to stand up toward the wearer's skin side when the diaper 10 is worn.

Further, as illustrated in FIG. 7, in the diaper 10, in addition to the thread-form elastic members 29a, a thread-form elastic member 29b is fixed in its stretched state inside the sheet material 27 folded into two and forming the leak-proof cuff 26. The elastic member 29b is arranged between the joined region 28 and the thread-form elastic members 29a in the leak-proof cuff 26, and is arranged in a portion, in the article longitudinal direction X, of the leak-proof cuff 26. The thread-form elastic member 29b is arranged at a position outward, in the article lateral direction Y, of a later-described thread-form elastic member 29c arranged at a lateral side of the absorbent member 23 in a spread-out state of the diaper 10.

Further, as illustrated in FIG. 7, in the diaper 10, an elastic member 29c is provided to each of the absorbent member 23's lateral side edge portions, which extend along the article longitudinal direction X, and is arranged in its stretched state along the lateral side edge portion. The contractile force of the respective elastic members 29c causes the absorbent core 24's lateral side edge portions, which extend along the longitudinal direction X, to stand up toward the wearer's skin side. The elastic member 29c is arranged in a portion, in the article longitudinal direction X, of the absorbent core 24. The elastic member 29c is located between the core-wrap sheet 25 constituting the absorbent member 23 and the topsheet 21 and is joined to both sheets. The contractile force of the elastic members 29c causes the absorbent member 23 located in the absorbent core 24's lateral side edge portions, which extend along the longitudinal direction X, to stand up toward the wearer's skin side, and also, the contractile force of the elastic members 29c causes the absorbent member 23's lateral sides, which are along the article longitudinal direction X, to easily contact with the wearer's legs. This promotes restoration of the absorbent core in the article lateral direction Y after the absorbent core 24 has been compressed inwardly in the article lateral direction Y by the wearer's movement.

The constituent materials in the various sections of the aforementioned disposable diaper 10 are described below.

For the constituent materials in the various sections, materials ordinarily used in this technical field can be used without particular limitation.

For example, for the topsheet 21, it is possible to use a hydrophilic liquid-permeable nonwoven fabric or a porous film. For the backsheet 22, it is possible to use a liquid-impermeable material or water-repellent material. For the liquid-impermeable material, it is possible to use, for example, a resin film or a laminate of a resin film and nonwoven fabric. For the water-repellent material, a water-repellent nonwoven fabric can be used, for example. For the water-repellent nonwoven fabric, it is possible to use a later-described nonwoven fabric used for the sheet material 27 forming the leak-proof cuff 26. For the core-wrap sheet 25, it is possible to use, for example, tracing paper (tissue paper) made by a wet papermaking method or a liquid-permeable nonwoven fabric.

For the sheet material 27 forming the leak-proof cuff 26, it is possible to use, for example, a multilayer-structure composite nonwoven fabric including spun-bonded/melt-blown/spun-bonded layers, a spun-bonded nonwoven fabric, a heat-bonded nonwoven fabric, or an air-through nonwoven fabric. From the viewpoint of softness and water resistance, a multilayer-structure nonwoven fabric made of spun-bonded and melt-blown layers is preferable.

The inner sheet 31 and outer sheet 32 forming the outer cover 30 are preferably made of the same or different air-permeable sheets, such as nonwoven fabrics manufactured according to one of various methods. For example, spun-bonded nonwoven fabrics are preferably used for the inner sheet 31 and outer sheet 32.

The thread-form elastic members 29a, 29b, 29c used in the absorbent assembly 20 may be shaped preferably as rubber threads or rubber bands with a predetermined width (such as rubber tapes), and particularly preferably as rubber threads. Similarly, the thread-form elastic members 33 (waist elastic members 33W, leg elastic members 33L, and below-waist elastic members 33D) used in the outer cover 30 may be shaped preferably as rubber threads or rubber bands with a predetermined width (such as rubber tapes), and particularly preferably as rubber threads. Examples of materials for the elastic members 29a, 29b, 29c and the elastic members 33 (waist elastic members 33W, leg elastic members 33L, and below-waist elastic members 33D) include natural rubber, synthetic rubber such as styrene-butadiene, butadiene, isoprene and neoprene, EVA, extensible polyolefins, and urethane.

The following describes the actions and effects of using the aforementioned diaper 10 according to the present embodiment of the invention.

Figure 9:
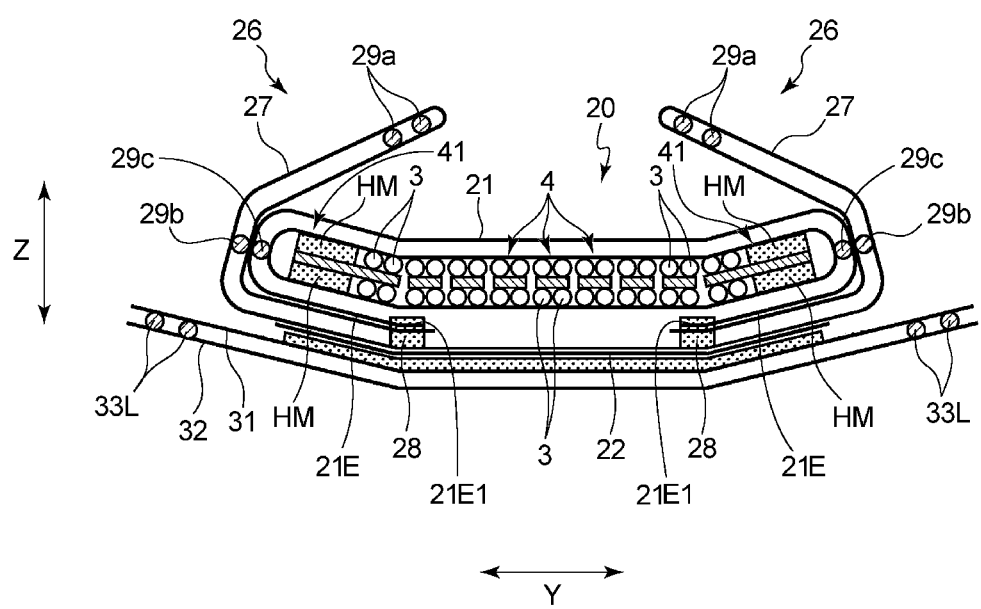
FIG. 9 is a cross-sectional view illustrating a state in which the diaper of FIG. 7 has been deformed.

In the diaper 10, as illustrated in FIGS. 1 and 2, the absorbent core 24 is formed of a sheet-like article 1 including a plurality of unit portions 40 arranged in the longitudinal direction (x1 direction), each of the plurality of unit portions including a plurality of absorbent units 4 that are arranged in the lateral direction (y1 direction) and that include a water-absorbent polymer 3. In each of the unit portions 40 of the sheet-like article 1 which is the absorbent core 24, the absorbent units 4 are arranged such that the absorbent unit's longitudinal direction (x1 direction) is oriented in the article longitudinal direction X of the diaper 10. Thus, in the diaper 10, it is possible to improve the softness of the absorbent core 24 and reduce the thickness of the absorbent core 24. Further, as illustrated in FIGS. 3 and 4, the sheet-like article 1 forming the absorbent core 24 includes a pair of longitudinal joined regions 41, 41 arranged at respective lateral sides which are along the longitudinal direction (x1 direction), a pair of lateral joined regions 42, 42 arranged at respective end portions in the longitudinal direction (x1 direction), and intermediate lateral joined regions 43, 43 arranged between the pair of lateral joined regions 42, 42; and the sheet-like article is joined at these positions to a core-wrap sheet 25 by a hot-melt adhesive HM. Thus, for example, even when an external force is applied inwardly, in the article lateral direction Y, from the wearer's legs when the diaper 10 is worn and the absorbent units 4 gather toward the center in the article lateral direction Y (lateral direction (y1 direction)) as illustrated in FIG. 9, the absorbent units 4 that have gathered toward the center can easily return to the outward side in the article lateral direction Y (lateral direction (y1 direction)). As a result, it is possible to suppress the uncomfortable feel caused by the central bulging that may be created when the absorbent units 4 gather toward the center in the article lateral direction Y (lateral direction (y1 direction)) and also suppress side leakage from both lateral sides which extend along the article longitudinal direction X (longitudinal direction (x1 direction)). As described above, with the diaper 10 according to the present embodiment of the invention, it is possible to achieve excellent softness and improve fittability and leakage preventability.

Further, as illustrated in FIG. 7, in the sheet-like article 1 which is the absorbent core 24 in the diaper 10, in a state after swelling, the water-absorbent polymer particles 3 swell beyond the long base portion 2's lateral side edge portions 2s (cf. the water-absorbent polymer particle 3a in FIG. 6), and the positions, in the thickness direction (Z direction; z1 direction), of the water-absorbent polymer particles 3 in each long base portion 2 are varied from the positions thereof before absorbing a liquid. Thus, even when the water-absorbent polymer particles 3, 3—which have swollen beyond the lateral side edge portions 2s of the respective long base portions 2 of adjacent absorbent units 4, 4—come into contact with one another when the water-absorbent polymer particles 3 absorb body fluid and swell as illustrated in FIG. 6, the adjacent absorbent units 4, 4 are facilitated to move freely in the thickness direction (Z direction; z1 direction), which makes it possible to lessen collision between the swollen water-absorbent polymer particles 3, 3 and reduce pressure applied to the swollen water-absorbent polymer particles 3, thus suppressing inhibition of absorption of body fluid by the water-absorbent polymer particles 3. Thus, in the sheet-like article 1 which is the absorbent core 24, the water-absorbent polymer particles 3 are less likely to cause swelling inhibition when the water-absorbent polymer particles 3 absorb body fluid and swell, and it is possible to make full use of the absorption performance of the water-absorbent polymer particles 3. Thus, the absorption performance of the diaper 10 is easily improved. Particularly, in the sheet-like article 1 of the diaper 10, since there is no intervening member present between the absorbent units 4, 4 adjacent to one another, the absorbent units 4 can move easily, thus making it even more easy to achieve the aforementioned effects.

In the sheet-like article 1 of the diaper 10, from the viewpoint of further suppressing swelling inhibition of the water-absorbent polymer particles 3 by causing the water-absorbent polymer particles 3 in a swollen state to swell beyond the lateral side edge portions 2s of the long base portions 2 and cause adjacent absorbent units 4, 4 to move freely in the thickness direction (Z direction; z1 direction), it is preferable that, in a state before use as illustrated in FIG. 5, the water-absorbent polymer particles 3 are arranged in the vicinity of the long base portion 2's lateral side edge portions 2s which extend along the longitudinal direction (x1 direction), and more preferably, the water-absorbent polymer particles 3 protrude beyond the long base portion 2's lateral side edge portions 2s (cf. the water-absorbent polymer particle 3b illustrated in FIG. 5).

Particularly, in the front unit portion 40A, the crotch unit portion 40C, and the rear unit portion 40B of the sheet-like article 1, from the viewpoint of further suppressing swelling inhibition of the water-absorbent polymer particles 3 by causing the water-absorbent polymer particles 3 in a swollen state to swell beyond the lateral side edge portions 2s of the long base portions 2 and cause adjacent absorbent units 4, 4 to move freely in the thickness direction (Z direction; z1 direction), it is preferable that the distance between the long base portion 2's both lateral side edge portions 2s, 2s that extend along the longitudinal direction (x1 direction) is greater than the average particle size of the water-absorbent polymer particles 3 in a state before use (before swelling), and is smaller than the average particle size of the water-absorbent polymer particles 3 in a state after swelling. Herein, "the distance between the long base portion 2's both lateral side edge portions 2s, 2s" is synonymous with the width W of the long base portion 2. It is preferable that the average particle size of the water-absorbent polymer particles 3 in a state before use (before swelling) is preferably 20 μm or greater, more preferably 200 μm or greater, and preferably 700 μm or less, more preferably 500 μm or less, and more specifically, preferably from 20 to 700 μm, more preferably from 200 to 500 μm. On the other hand, the average particle size of the water-absorbent polymer 3 in a state after swelling is preferably 200 μm or greater, more preferably 800 μm or greater, and preferably 3000 μm or less, more preferably 2000 μm or less, and more specifically, preferably from 200 to 3000 μm, more preferably from 800 to 2000 μm. The average particle size of the water-absorbent polymer particles 3 is found according to the following measurement method.

{Method for Measuring Average Particle Size d1 of Water-Absorbent Polymer Particles in a State Before Use}

The average particle size d1 in a state before use was measured using water-absorbent polymer particles before use by observing the diameter or major axis of the water-absorbent polymer particles with an optical microscope. Herein, "diameter" applies to cases where the water-absorbent polymer particle is spherical, and "major axis" applies to cases where the water-absorbent polymer particle is odd-formed, such as rhombic, rectangular, cluster-like, or football-shaped. The diameter or major axis is measured for a total of 50 water-absorbent polymer particles, and the number-average particle size is defined as the average particle size d1 of the water-absorbent polymer particles in a state before use.

{Method for Measuring Average Particle Size d2 of Water-Absorbent Polymer Particles in a State After Swelling}

The average particle size d2 in a state after swelling was measured by: immersing the sheet-like article 1 in a physiological saline solution (0.9 mass % sodium chloride aqueous solution) whose temperature has been adjusted to 25° C.; taking the sheet-like article 1 out from the physiological saline solution after 1 hour from the start of immersion; draining the sheet-like article by hanging the same in a vertical state for 30 minutes; and then observing, with an optical microscope, the diameter or major axis of the water-absorbent polymer particles on the surface of the long base portions 2. Herein, "diameter" applies to cases where the water-absorbent polymer particle is spherical, and "major axis" applies to cases where the water-absorbent polymer particle is odd-formed, such as rhombic, rectangular, cluster-like, or football-shaped. The diameter or major axis is measured for a total of 50 water-absorbent polymer particles, and the number-average particle size can be defined as the average particle size of the water-absorbent polymer particles in a state after swelling.

Figure 10:
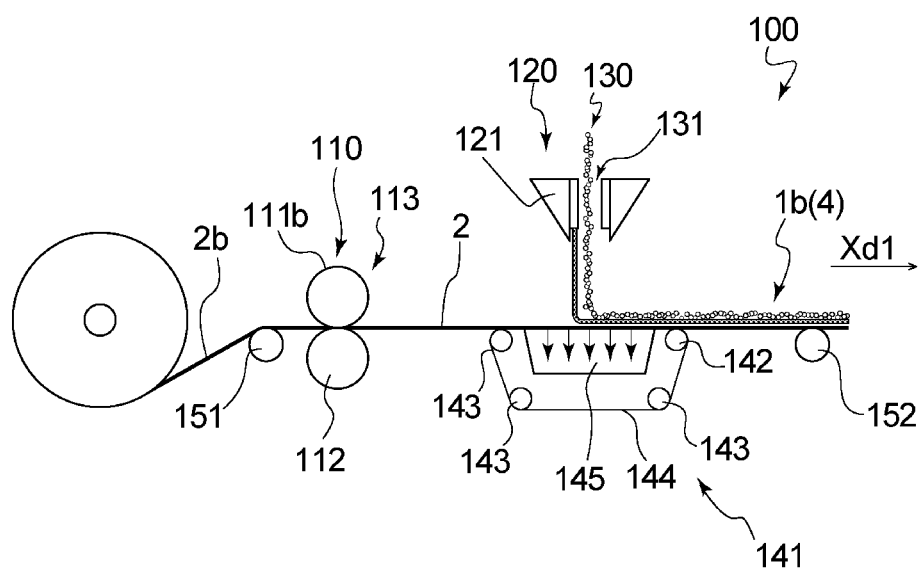
FIG. 10 is a schematic diagram illustrating an embodiment of a device for manufacturing a sheet-like article, which is an absorbent core of the diaper illustrated in FIG. 1.
Figure 11:
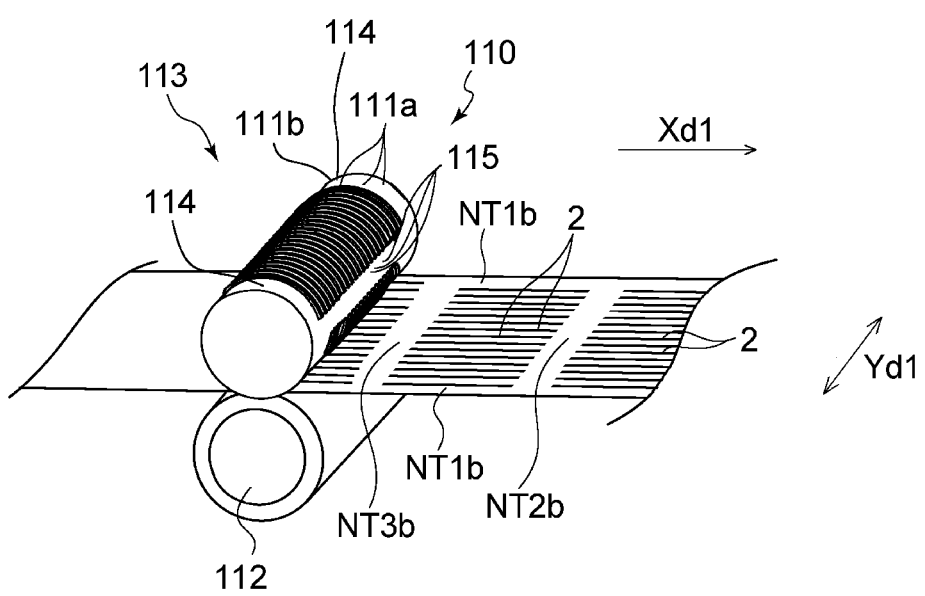
FIG. 11 is a schematic perspective view of a base sheet cutting unit provided in the manufacturing device illustrated in FIG. 10.

Next, a preferred embodiment of a method for manufacturing a sheet-like article 1 used in a disposable diaper 10, which is an embodiment of the invention, is described with reference to FIGS. 10 and 11 according to an example of manufacturing the sheet-like article 1 configured as above. FIG. 10 illustrates a manufacturing device 100 suitably used for the manufacturing method of the present embodiment. FIG. 11 is a schematic perspective view of a base sheet cutting unit 110 provided in the manufacturing device 100 illustrated in FIG. 10.

The manufacturing device 100 of the present embodiment includes, in the following order from the upstream side toward the downstream side of the manufacturing steps: a base sheet cutting unit 110; an adhesive application unit 120; and a water-absorbent polymer dispersion unit 130. Note that, although the manufacturing device 100 illustrated in FIG. 10 uses a device in which the adhesive application unit 120 and the water-absorbent polymer dispersion unit 130 are integrated, the adhesive application unit 120 and the water-absorbent polymer dispersion unit 130 do not have to be integrated. In the integrated device, the adhesive application unit 120 is arranged on the upstream side of the device, and the water-absorbent polymer dispersion unit 130 is arranged on the downstream side of the integrated device.

The base sheet cutting unit 110 is a region for forming a plurality of long base portions 2—which constitute respective precursors of the sheet-like article 1's unit portions 40 (the front unit portion 40A, the crotch unit portion 40C, and the rear unit portion 40B)—by cutting a continuous base sheet 2b, which is the material for the long base portions 2. Any one of various known cutting devices can be used without particular limitation for cutting the base sheet 2b. As illustrated in FIG. 10, this manufacturing device 100 employs a set of a cutting device 113, as illustrated in FIG. 11, including a rotary die 111b having a plurality of cutter blades 111a, 111a, 111a, . . . arranged on the circumferential surface thereof, and a receiving roller 112 that has a flat circumferential surface and that is arranged in opposition to the rotary die 111b.

The cutting device 113 is a cutting device 113 including: a plurality of cutter blades 111a, 111a, 111a, . . . corresponding to the front unit portion 40A, the crotch unit portion 40C, and the rear unit portion 40B in the transporting direction (Xd1 direction) of the base sheet 2b as illustrated in FIG. 11; and a receiving roller 112 that is arranged in opposition common to the cutter blades 111a, 111a, 111a, . . . and that has a flat circumferential surface. The cutter blades 111a, 111a, 111a, . . . of the cutting device 113 are arranged so as to match the direction (Yd1 direction) orthogonal to the transporting direction (Xd1 direction) of the continuous base sheet 2b. The distance between the cutter blades 111a, 111a adjacent to one another in the orthogonal direction (Yd1 direction) corresponds to the width W (cf. FIG. 4) of each long base portion 2 to be formed in the front unit portion 40A, the crotch unit portion 40C, and the rear unit portion 40B. Note that, for cutting the base sheet 2b, it is possible to use: a cutting device employing a shear-cut method in which cutting is achieved by rubbing the side surfaces of an upper blade and a lower blade against one another; or a laser device that performs melting-and-cutting by the irradiation of a laser beam.

As in the sheet-like article 1 illustrated in FIGS. 3 and 4, in cases where the sheet-like article 1 includes a pair of longitudinal non-slit regions NT1, NT1 in the respective lateral sides along the longitudinal direction (x1 direction), for example, the circumferential surface of the roller may be provided with longitudinal non-arrangement sections 114, where no cutter blade 111a is arranged, formed at respective end portions in the roller's axial direction, as illustrated in FIG. 11.

Further, as in the sheet-like article 1 illustrated in FIGS. 3 and 4, in cases where the sheet-like article 1 includes a pair of lateral non-slit regions NT2, NT2 at respective end portions in the longitudinal direction (x1 direction) and intermediate lateral non-slit regions NT3, NT3 between the pair of lateral non-slit regions NT2, NT2, for example, the circumferential surface of the roller may be provided with a plurality of lateral non-arrangement sections 115, where no cutter blade 111a is arranged, formed with intervals therebetween in the circumferential direction, as illustrated in FIG. 11. The length of the arc (the length in the circumferential direction) of the lateral non-arrangement sections 115 on the outer circumference of the rotating cutter blades 111a is set to a length corresponding to the length, in the longitudinal direction (x1 direction), of the respective lateral non-slit regions NT2 and the intermediate lateral non-slit regions NT3 of the sheet-like article 1 illustrated in FIGS. 3 and 4.

Note that the length of the arc in each section excluding the longitudinal non-arrangement sections 114 and lateral non-arrangement sections 115 in the outer circumference of each rotating cutter blade 111a corresponds to the length L1 (cf. FIG. 3), in the longitudinal direction (x1 direction), of each long base portion 2 in the front unit portion 40A, the crotch unit portion 40C, and the rear unit portion 40B of the sheet-like article 1 illustrated in FIGS. 3 and 4.

The adhesive application unit 120, which is located downstream of the base sheet cutting unit 110, is a region for applying a hot-melt adhesive HM on the surface of one face (e.g., the face that becomes the skin-facing surface) of the respective long base portions 2 constituting the precursors of the unit portions 40 (the front unit portion 40A, the crotch unit portion 40C, and the rear unit portion 40B), the pair of longitudinal non-slit regions NT1, NT1, the pair of lateral non-slit regions NT2, NT2, and the two intermediate lateral non-slit regions NT3, NT3. As illustrated in FIG. 10, in the manufacturing device 100, the adhesive application unit 120 includes an application head 121. Any one of various known application devices can be used without particular limitation for the application head 121.

In the orthogonal direction (Yd1 direction), the entire width of the application head 121 is slightly shorter than the entire width (the length in the lateral direction (y1 direction)) of the sheet-like article 1, and is a width subtracting the length, in the lateral direction (y1 direction), of the pair of non-application portions 44, 44 from the length, in the lateral direction (y1 direction), of the sheet-like article 1.

The application head 121 is formed so that the hot-melt adhesive HM can be applied to the surface of the pair of longitudinal non-slit regions NT1, NT1 located in the respective lateral sides, in the lateral direction (y1 direction), of the sheet-like article 1.

Further, the application head 121 is formed so that it is possible to apply, between the pair of longitudinal non-slit regions NT1, NT1 of the sheet-like article 1, the hot-melt adhesive HM continuously, in the transporting direction (Xd1 direction), in the order of the lateral non-slit region NT2, the precursor of the front unit portion 40A, the intermediate lateral non-slit region NT3, the precursor of the crotch unit portion 40C, the intermediate lateral non-slit region NT3, the precursor of the rear unit portion 40B, and the lateral non-slit region NT2, for example. The application head 121 configured as above is arranged above one face (e.g., the face that becomes the skin-facing surface) of the base sheet 2b (sheet-like article 1) at a distance therefrom.

The water-absorbent polymer dispersion unit 130, which is located downstream of the adhesive application unit 120, is a region for dispersing water-absorbent polymer particles 3 on the surface of the one face (e.g., the face that becomes the skin-facing surface) of the long base portions 2 constituting the precursors of the unit portions 40 (the front unit portion 40A, the crotch unit portion 40C, and the rear unit portion 40B), to thereby form absorbent units 4. As illustrated in FIG. 10, in the manufacturing device 100, the water-absorbent polymer dispersion unit 130 includes a water-absorbent polymer introduction unit 131. For the water-absorbent polymer introduction unit 131, any one of various known introduction devices can be used without particular limitation.

In the orthogonal direction (Yd1 direction), the entire width of the water-absorbent polymer introduction unit 131 is set to a width corresponding to the width (length in the lateral direction (y1 direction)) of the unit portions 40 (the front unit portion 40A, the crotch unit portion 40C, and the rear unit portion 40B) of the sheet-like article 1. The water-absorbent polymer introduction unit 131 configured as above is arranged above the one face (e.g., the face that becomes the skin-facing surface) of the base sheet 2b (sheet-like article 1) at a distance therefrom.

In the manufacturing device 100 illustrated in FIG. 10, a vacuum conveyor 141 is arranged at a position opposing the device in which the adhesive application unit 120 and the water-absorbent polymer dispersion unit 130 are integrated, and on the lower surface side of the base sheet 2b being transported. The vacuum conveyor 141 includes: an endless air-permeable belt 144 that bridges a drive roller 142 and a plurality of driven rollers 143; and a vacuum box 145 arranged at a position opposing the aforementioned integrated device across the air-permeable belt 144. The base sheet 2b, in which the plurality of long base portions 2 have been formed by the base sheet cutting unit 110, is introduced onto the vacuum conveyor 141.

The manufacturing device 100 illustrated in FIG. 10 includes: a drive roller 151 that pays out the base sheet 2b from an original textile roll of the continuous base sheet 2b; and a drive roller 152, at the most downstream side, that transports a precursor 1b of a sheet-like article 1 which has been manufactured.

In the sheet-like article 1, the water-absorbent polymer particles 3 are fixed to the surfaces of both faces of the long base portions 2. Thus, the manufacturing device includes, on the downstream side of the integrated device in which the adhesive application unit 120 and the water-absorbent polymer dispersion unit 130 are integrated: an inversion roller (not illustrated) that flips the sheet; a separate adhesive application unit (not illustrated) for applying a hot-melt adhesive HM to the surface of the other face of the sheet-like article 1; and a separate water-absorbent polymer dispersion unit (not illustrated) for dispersing the water-absorbent polymer particles 3 onto the surface of the other face of the long base portions 2. The separate adhesive application unit (not illustrated) and the separate water-absorbent polymer dispersion unit (not illustrated) have the same configuration as the adhesive application unit 120 and the water-absorbent polymer dispersion unit 130.

Next, a method for manufacturing sheet-like articles 1 continuously using the aforementioned manufacturing device 100 of the present embodiment, i.e., an embodiment of a method for manufacturing a sheet-like article 1 used in a disposable diaper 10 which is an embodiment of the invention, will be described. In the method for manufacturing sheet-like articles 1 by using the manufacturing device 100, first, negative pressure is generated inside the vacuum box 145 by activating an evacuation device connected thereto.

Next, the drive rollers 151 and 152 are driven, the cutting device 113 and the air-permeable belt 144 are rotated, and the vacuum conveyor 141 is activated. Then, the base sheet 2b is paid out by the drive roller 151 from the original textile roll of the continuous base sheet 2b, and the base sheet is supplied between the receiving roller 112 and the roller including the plurality of cutter blades 111a in the cutting device 113 of the base sheet cutting unit 110. Thus, the continuous base sheet 2b is cut, thereby forming the precursors of the unit portions 40 (the front unit portion 40A, the crotch unit portion 40C, and the rear unit portion 40B) with spaces therebetween in the transporting direction (Xd1 direction), each unit portion including a plurality of long base portions 2 arranged side by side in the orthogonal direction (Yd1 direction) (cutting step).

In the embodiment using the manufacturing device 100, the lateral non-arrangement sections 115 where no cutter blade 111a is arranged are formed on the circumferential surface of the roller. This thereby forms, in the continuous base sheet 2b being transported: lateral non-cut portions NT2b corresponding to the lateral non-slit regions NT2 formed at the respective end portions, in the longitudinal direction (x1 direction), of the sheet-like article 1; and intermediate lateral non-cut portions NT3b corresponding to the intermediate lateral non-slit regions NT3 arranged between the unit portions 40 adjacent to one another in the longitudinal direction (x1 direction).

In the present embodiment employing the manufacturing device 100, longitudinal non-arrangement sections 114 where no cutter blade 111a is arranged are formed on the circumferential surface in both end portions in the roller's axial direction. This thereby forms, at the respective lateral sides, along the transporting direction (Xd1 direction), of the continuous base sheet 2b being transported, a pair of longitudinal non-cut portions NT1b, NT1b each having the same length as the length, in the lateral direction (y1 direction), of the respective longitudinal non-slit regions NT1, NT1.

Next, a hot-melt adhesive HM is applied on the surface of one face of the long base portions 2 that have been formed in the cutting step and that constitute the precursors of the unit portions 40 (the front unit portion 40A, the crotch unit portion 40C, and the rear unit portion 40B) (adhesive application step). In the present embodiment employing the manufacturing device 100, while the base sheet 2b is being transported by the vacuum conveyor 141 and is located above the vacuum box 145, the application head 121 of the adhesive application unit 120 applies the hot-melt adhesive HM.

Preferably, the hot-melt adhesive HM is applied continuously along the longitudinal direction (x1 direction) on the surface of one face of the pair of longitudinal non-cut portions NT1b, NT1b located at the respective lateral sides along the longitudinal direction (x1 direction). The hot-melt adhesive HM is also applied to the surface of the long base portions 2 in the front unit portion 40A, the rear unit portion 40B, and the crotch unit portion 40C, and on the surface in the lateral non-cut portions NT2b and the intermediate lateral non-cut portions NT3b at locations corresponding to locations continuous from the respective long base portions 2 in the longitudinal direction (x1 direction). As a result, on the surface of one face of the respective long base portions 2 in the unit portions 40, the hot-melt adhesive HM is applied continuously in the longitudinal direction (x1 direction) and with spacings therebetween in the lateral direction (y1 direction). Also, on the surface of the lateral non-cut portions NT2$b$ and the intermediate lateral non-cut portions NT3$b$, the hot-melt adhesive HM is applied with spacings therebetween in the lateral direction (y1 direction).

Next, water-absorbent polymer particles 3 are dispersed on the hot-melt adhesive HM applied on the surface of the one face (upper face) of the long base portions 2 formed in the base sheet 2$b$ (water-absorbent polymer particle dispersion step). In the present embodiment employing the manufacturing device 100, while the long base portions 2—which constitute the precursors of the unit portions 40 (the front unit portion 40A, the crotch unit portion 40C, and the rear unit portion 40B) having the hot-melt adhesive HM applied on the surface of the one face in the adhesive application step—are being transported by the vacuum conveyor 141 and are located above the vacuum box 145, the water-absorbent polymer introduction unit 131 of the water-absorbent polymer dispersion unit 130 disperses the water-absorbent polymer particles 3 only on the hot-melt adhesive HM applied on the surface of the one face of the long base portions 2 arranged side by side in the precursors of the unit portions 40. Note, however, that the water-absorbent polymer particles 3 are not dispersed on the pair of longitudinal non-cut portions NT1$b$, NT1$b$, the lateral non-cut portions NT2$b$, and the intermediate lateral non-cut portions NT3$b$. Dispersing the water-absorbent polymer particles 3, as described above, forms the unit portions 40 (the front unit portion 40A, the crotch unit portion 40C, and the rear unit portion 40B) including a plurality of absorbent units 4, wherein the water-absorbent polymer particles 3 are fixed to the surface of the respective long base portions 2 by means of the hot-melt adhesive HM.

In the sheet-like article 1, the water-absorbent polymer particles 3 are fixed to the surfaces of both faces of the respective long base portions 2. Thus, the manufacturing device 100 illustrated in FIG. 10 can be used to manufacture this sheet-like article by: first fixing the water-absorbent polymer particles 3 to the surface of one face of the respective long base portions 2; then flipping the sheet-like article over with an inversion roller; then applying a hot-melt adhesive HM onto the surface of the other face of the sheet-like article 1 using a separate adhesive application unit (not illustrated); and then dispersing and fixing water-absorbent polymer particles 3 onto the surface of the other face of the respective long base portions 2 by using a separate water-absorbent polymer dispersion unit (not illustrated).

A precursor 1$b$ of the sheet-like article 1 is formed according to the above. In the precursor 1$b$ of the sheet-like article 1 formed as above, the absorbent units 4 formed in the front unit portion 40A, the crotch unit portion 40C, and the rear unit portion 40B are arranged such that their longitudinal direction (x1 direction) is oriented in the transporting direction (Xd1 direction).

Then, the precursor 1$b$ of the sheet-like article 1 is transported downstream by the drive roller 152, and, using a known cutting device (not illustrated), the precursor is cut at every position of the lateral non-cut portion NT2$b$. In this way, sheet-like articles 1 are manufactured continuously. With the embodiment employing the manufacturing device 100, it is possible to manufacture sheet-like articles 1 stably and efficiently.

The disposable diaper 10 which is an embodiment of the invention can be manufactured similarly to known methods for manufacturing pull-on disposable diapers according to the so-called cross-flow system, except that the sheet-like article 1 manufactured by using the manufacturing device 100 is used as the absorbent core 24. For example, while continuously transporting sheet-like articles 1 such that their longitudinal direction is in the flow direction (longitudinal flow), the entirety of each sheet-like article is covered by a continuous core-wrap sheet 25, to form a continuous strip of absorbent members 23 in which the sheet-like articles 1 are arranged intermittently in the flow direction. In each absorbent member 23 formed as above, the sheet-like article 1 is joined to the core-wrap sheet 25 at the pair of longitudinal joined regions 41, 41, the pair of lateral joined regions 42, 42, and the intermediate lateral joined regions 43. Then, the upper surface of the continuous strip of the absorbent members 23 is covered by a topsheet member, which is formed by fixing sheet materials 27—each having continuous thread-form elastic members 29$a$, 29$b$, 29$c$ arranged therein and each having been folded—to the respective lateral sides of a continuous topsheet 21. Also, the lower surface of the continuous strip of the absorbent members 23 is covered by a continuous backsheet 22. Then, both lateral sides, of the topsheet member, which extend along the flow direction (longitudinal flow) are wrapped downward onto the lower surface side of the continuous strip of the absorbent members 23, and these constituent members are fixed together. Then, the sheet-like articles 1 adjacent to one another in the flow direction (longitudinal flow) are cut therebetween, to continuously manufacture absorbent assemblies 20 in the flow direction (longitudinal flow). Thereafter, each of the absorbent assemblies 20 is turned 90 degrees, and is fixed by an adhesive, such as a hot-melt adhesive, onto an inner sheet 31 of a continuous outer cover 30 manufactured in a separate process, to thereby form a continuous strip of diapers 10. Next, leg holes are formed inside annular portions annularly surrounded by leg elastic members 33L in the continuous strip of the outer cover 30 on which the absorbent assemblies 20 have been arranged. Next, both lateral sides, in the flow direction, of the continuous strip of the outer cover 30 are superposed on one another, to fold the continuous strip of the outer cover 30 and each of the absorbent assemblies 20 into two. Thereafter, side seals S are formed intermittently, and then cutting is performed at each of the side seals S, to thereby continuously manufacture diapers 10.

The invention is not limited to the foregoing embodiments and can be modified as appropriate.

As illustrated in FIGS. 3 and 4, the aforementioned sheet-like article 1, which is the absorbent core 24 of the diaper 10, is provided with the front unit portion 40A, the crotch unit portion 40C, and the rear unit portion 40B as the plurality of unit portions 40 arranged in the sheet-like article 1. The sheet-like article, however, only needs to include two or more unit portions as the plurality of unit portions. Further, the length, in the longitudinal direction (x1 direction), is made uniform among the front unit portion 40A, the crotch unit portion 40C, and the rear unit portion 40B, but the length in the longitudinal direction (x1 direction) may be non-uniform.

Further, in the sheet-like article 1 of the diaper 10, as illustrated in FIG. 5, the water-absorbent polymer particles 3 are fixed to the surface of both faces (e.g., the face that becomes the skin-facing surface and the face that becomes the non-skin-facing surface) of the respective long base portions 2. The water-absorbent polymer particles 3, however, only need to be fixed on the surface of the long base portions 2 on at least one of the two faces of the sheet-like article 1.

Further, in the sheet-like article 1 of the diaper 10, as illustrated in FIG. 5, the hot-melt adhesive HM is applied to the surface of both faces (e.g., the face that becomes the skin-facing surface and the face that becomes the non-skin-facing surface) of the respective long base portions 2. The hot-melt adhesive HM, however, only needs to be applied to at least one of the two faces of the sheet-like article 1.

In the diaper 10, the pair of longitudinal joined regions 41, 41, the pair of lateral joined regions 42, 42, and the two intermediate lateral joined regions 43, 43 are joined to the constituent member of the diaper 10 by employing a hot-melt adhesive HM. Joining with the constituent member of the diaper 10, however, may be achieved by employing a different joining means, such as heat embossing, for example.

In the diaper, as illustrated in FIGS. 3 and 4, the pair of lateral joined regions 42, 42 and the two intermediate lateral joined regions 43, 43 are connected to the pair of longitudinal joined regions 41, 41. The pair of lateral joined regions 42, 42 and the two intermediate lateral joined regions 43, 43, however, do not have to be connected to the pair of longitudinal joined regions 41, 41.

The front unit portion 40A, the crotch unit portion 40C, and the rear unit portion 40B arranged in the sheet-like article 1 serving as the absorbent core 24 are spaced uniformly, but the unit portions may be arranged at different intervals.

Further, a so-called second sheet arranged between the topsheet 21 and the absorbent core 24 may serve as the constituent member that constitutes the diaper 10 and is adjacent on at least either an upper side or a lower side in the thickness direction Z and to which the pair of longitudinal joined regions 41, 41, the pair of lateral joined regions 42, 42, and the intermediate lateral joined regions 43, 43 of the sheet-like article 1, which forms the absorbent core 24, are joined.

Other than the aforementioned disposable diaper 10, the absorbent article of the invention may be an article used for absorbing and retaining excreted body fluid such as urine or menstrual blood. Absorbent articles include, for example, open-type disposable diapers, sanitary napkins, and incontinence pads, but are not limited thereto, and widely encompass articles used for absorbing liquids excreted from the human body.

In relation to the foregoing embodiments, the following absorbent articles are further disclosed.

{1}

An absorbent article comprising an absorbent assembly including a topsheet, a backsheet, and an absorbent core interposed between the topsheet and the backsheet, the absorbent article having an article longitudinal direction extending from a front region to be arranged on a front side of a wearer toward a rear region to be arranged on a rear side of the wearer, and an article lateral direction orthogonal to the article longitudinal direction, wherein:

the absorbent core is formed of a sheet-like article including a plurality of absorbent units, each of the plurality of absorbent units including a long base portion having a lateral direction, a longitudinal direction that is longer than the lateral direction, and a thickness direction, and water-absorbent polymer particles that are fixed to a surface of at least one face of the long base portion, the absorbent units being arranged such that the absorbent unit's longitudinal direction is oriented in the article longitudinal direction;

the sheet-like article includes a plurality of unit portions arranged in the longitudinal direction, each of the plurality of unit portions including a plurality of the absorbent units arranged side by side in the lateral direction;

the sheet-like article includes a pair of longitudinal joined regions extending in the longitudinal direction at respective lateral sides which are along the longitudinal direction, a pair of lateral joined regions extending in the lateral direction at respective end portions in the longitudinal direction, and an intermediate lateral joined region extending in the lateral direction between the lateral joined regions; and the sheet-like article is joined at the longitudinal joined regions, the lateral joined regions, and the intermediate lateral joined region to a constituent member that constitutes the absorbent article and that is adjacent on at least either an upper side or a lower side in the thickness direction, and each of the unit portions includes a section in which neither the upper side nor the lower side thereof in the thickness direction is joined to the constituent member.

{2}

The absorbent article as set forth in clause {1}, wherein:

the unit portions are arranged with a space therebetween in the longitudinal direction; and the intermediate lateral joined region is arranged between the unit portions that are adjacent to one another in the longitudinal direction.

{3}

The absorbent article as set forth in clause {1} or {2}, wherein the water-absorbent polymer particles are not arranged in the longitudinal joined regions, the lateral joined regions, and the intermediate lateral joined region.

{4}

The absorbent article as set forth in any one of clauses {1} to {3}, wherein the longitudinal joined regions extend continuously in the longitudinal direction in the sheet-like article's respective lateral sides which are along the longitudinal direction.

{5}

The absorbent article as set forth in any one of clauses {1} to {4}, wherein a length, in the lateral direction, of the longitudinal joined region is greater than or equal to a length, in the lateral direction, of the long base portion.

{6}

The absorbent article as set forth in any one of clauses {1} to {5}, wherein a length, in the longitudinal direction, of the lateral joined region is longer than a length, in the longitudinal direction, of the intermediate lateral joined region.

{7}

The absorbent article as set forth in any one of clauses {1} to {6}, wherein the constituent member joined to the absorbent core at the longitudinal joined regions, the lateral joined regions, and the intermediate lateral joined region is joined to another constituent member constituting the absorbent article.

{8}

The absorbent article as set forth in clause {7}, wherein elastic members that contract around the wearer's legs are arranged in the other constituent member.

{9}

The absorbent article as set forth in any one of clauses {1} to {8}, wherein: the topsheet covers an entire surface of a skin-facing surface of the absorbent core, and includes extension portions extending outward, in the article lateral direction, from respective lateral side edge portions of the absorbent core;

the extension portions are folded back toward a non-skin-facing surface side of the absorbent core and cover the absorbent core's non-skin-facing surface;

a tip-end portion of each of the topsheet's folded-back extension portions is fixed to a constituent member of the absorbent article that is adjacent on the non-skin-facing surface side; and an elastic member is provided to and arranged along each of the absorbent core's lateral side edge portions, which extend along the longitudinal direction, and contractile force of the respective elastic members causes the absorbent core's lateral side edge portions, which extend along the longitudinal direction, to stand up toward the wearer's skin side.

{10}

The absorbent article as set forth in any one of clauses {1} to {9}, wherein the unit portions are spaced uniformly in the longitudinal direction.

{11}

The absorbent article as set forth in any one of clauses {1} to {10}, wherein the absorbent units are arranged so as not to intersect with one another.

{12}

The absorbent article as set forth in any one of clauses {1} to {11}, wherein the unit portion is formed by using a plurality of the absorbent units, each including the long base portion with a uniform width, and by arranging the absorbent units side by side in the lateral direction and parallel to the longitudinal direction of the sheet-like article.

{13}

The absorbent article as set forth in any one of clauses {1} to {12}, wherein, in the unit portion, there is no intervening member present between the absorbent units adjacent to one another in the lateral direction of the long base portion.

{14}

The absorbent article as set forth in any one of clauses {1} to {13}, wherein the percentage of an absorbent region formed by the unit portions to the entire sheet-like article is preferably 20% or greater, more preferably 50% or greater, and preferably 95% or less, more preferably 90% or less.

{15}

The absorbent article as set forth in any one of clauses {1} to {14}, wherein preferably 2 pieces or more, more preferably 10 pieces or more, and preferably 1000 pieces or fewer, more preferably 500 pieces or fewer, of the absorbent units are arranged in each of the unit portions.

{16}

The absorbent article as set forth in any one of clauses {1} to {15}, wherein:

non-slit regions are provided in the sheet-like article; and
the non-slit regions include
a pair of longitudinal non-slit regions extending in the longitudinal direction at the respective lateral sides which are along the longitudinal direction,
a pair of lateral non-slit regions extending in the lateral direction at the respective end portions in the longitudinal direction, and
two intermediate lateral non-slit regions extending in the lateral direction, each being provided between the unit portions adjacent to one another in the longitudinal direction.

{17}

The absorbent article as set forth in clause {16}, wherein the pair of longitudinal joined regions is arranged respectively in the pair of longitudinal non-slit regions on one face and the other face of the sheet-like article.

{18}

The absorbent article as set forth in clause {17}, wherein, in each of the longitudinal joined regions on the one face and the other face, an adhesive is applied along the respective longitudinal non-slit regions.

{19}

The absorbent article as set forth in clause {18}, wherein the adhesive applied to each of the longitudinal non-slit regions is arranged in a manner extending between both end portions, in the longitudinal direction, in each of the longitudinal non-slit regions.

{20}

The absorbent article as set forth in any one of clauses {17} to {19}, wherein the longitudinal non-slit regions on the one face and the other face each have a non-application portion, in which no adhesive is applied, formed at respective lateral-side outer edges along the longitudinal direction.

{21}

The absorbent article as set forth in clause {20}, wherein the non-application portion is arranged along the longitudinal joined region on the outermost side, in the lateral direction, of the longitudinal joined region.

{22}

The absorbent article as set forth in clause {20} or {21}, wherein the non-application portion is arranged substantially parallel to the longitudinal joined region on the outermost side, in the lateral direction, of the longitudinal joined region.

{23}

The absorbent article as set forth in any one of clauses {1} to {22}, wherein, as regards the ratio of a width of the longitudinal joined region to a width of the long base portion, the width of the longitudinal joined region is preferably 3 times or greater, more preferably 2 times or greater, and preferably 100 times or less, more preferably 10 times or less, the width of a single piece of the long base portion.

{24}

The absorbent article as set forth in any one of clauses {1} to {23}, wherein the width of the longitudinal joined region is preferably 3 mm or greater, more preferably 5 mm or greater, and preferably 50 mm or less, more preferably 10 mm or less.

{25}

The absorbent article as set forth in any one of clauses {1} to {24}, wherein the width of a single piece of the long base portion is preferably 0.3 mm or greater, more preferably 0.6 mm or greater, and preferably 10 mm or less, more preferably 2 mm or less.

{26}

The absorbent article as set forth in any one of clauses {16} to {25}, wherein the lateral joined region is arranged not only in the lateral non-slit region on one face but also in the lateral non-slit region on the other face.

{27}

The absorbent article as set forth in any one of clauses {16} to {26}, wherein the lateral joined region is constituted by applying an adhesive extending in the lateral direction in the lateral non-slit region.

{28}

The absorbent article as set forth in clause {27}, wherein, in each of the lateral joined regions on the one face and the other face, the adhesive is applied in the lateral direction along the respective lateral non-slit regions.

{29}

The absorbent article as set forth in clause {27} or {28}, wherein the adhesive applied to each of the lateral non-slit regions is arranged within each of the lateral non-slit regions in a manner extending between the pair of longitudinal joined regions.

{30}
The absorbent article as set forth in any one of clauses {27} to {29}, wherein the adhesive in each of the lateral joined regions on the one face and the other face is connected at both end portions, in the lateral direction, to the adhesive in the respective longitudinal joined regions.

{31}
The absorbent article as set forth in any one of clauses {27} to {30}, wherein, in each of the lateral joined regions, the adhesive is applied intermittently with spaces therebetween in the lateral direction in each of the lateral non-slit regions located at the respective end portions, in the longitudinal direction, of the sheet-like article.

{32}
The absorbent article as set forth in any one of clauses {1} to {31}, wherein the ratio of a width of the lateral joined region to a width of the intermediate lateral joined region is preferably 1.2 times or greater, more preferably 1.5 times or greater, and preferably 10 times or less, more preferably 5 times or less.

{33}
The absorbent article as set forth in any one of clauses {1} to {32}, wherein the width of the lateral joined region is preferably 5 mm or greater, more preferably 10 mm or greater, and preferably 100 mm or less, more preferably 30 mm or less.

{34}
The absorbent article as set forth in any one of clauses {1} to {33}, wherein the width of the intermediate lateral joined region is preferably 3 mm or greater, more preferably 5 mm or greater, and preferably 50 mm or less, more preferably 20 mm or less.

{35}
The absorbent article as set forth in any one of clauses {16} to {34}, wherein the intermediate lateral joined region is arranged in the intermediate lateral non-slit region on one face and the other face.

{36}
The absorbent article as set forth in any one of clauses {16} to {35}, wherein a plurality of the intermediate lateral joined regions are constituted by applying an adhesive extending in the lateral direction respectively in the two intermediate lateral non-slit regions.

{37}
The absorbent article as set forth in clause {36}, wherein the adhesive in each of the intermediate lateral joined regions on the one face and the other face is connected at both end portions, in the lateral direction, to the adhesive in the respective longitudinal joined regions.

{38}
The absorbent article as set forth in clause {17} or {37}, wherein the positions where the adhesive is applied intermittently in the lateral direction in each of the intermediate lateral joined regions respectively match, in the longitudinal direction, the positions where the adhesive is applied intermittently in the lateral direction in each of the lateral joined regions.

{39}
The absorbent article as set forth in any one of clauses {1} to {38}, wherein the sheet-like article's upper side and lower side, in the thickness direction, are joined to a core-wrap sheet in the longitudinal joined regions, the lateral joined regions, and the intermediate lateral joined region.

{40}
The absorbent article as set forth in any one of clauses {1} to {39}, wherein the percentage of a length, in the longitudinal direction, of a single piece of the long base portion constituting the unit portion to a length, in the longitudinal direction, of the sheet-like article is preferably 5% or greater, more preferably 10% or greater, and preferably 49% or less, more preferably 40% or less.

{41}
The absorbent article as set forth in any one of clauses {1} to {40}, wherein:
three of the unit portions are arranged in the longitudinal direction in the sheet-like article forming the absorbent core; and
the unit portions are arranged respectively in positions of the absorbent article's front region, crotch region, and rear region.

{42}
The absorbent article as set forth in any one of clauses {1} to {41}, wherein, in the sheet-like article, a front unit portion, a crotch unit portion, and a rear unit portion which are formed in the same shape are juxtaposed in the longitudinal direction.

{43}
The absorbent article as set forth in clause {42}, wherein the front unit portion, the crotch unit portion, and the rear unit portion are spaced uniformly in the longitudinal direction in the sheet-like article.

INDUSTRIAL APPLICABILITY

The invention is capable of providing an absorbent article having excellent softness and improved fittability and leakage preventability.

The invention claimed is:
1. An absorbent article comprising an absorbent assembly including a topsheet, a backsheet, and an absorbent core interposed between the topsheet and the backsheet, the absorbent article having an article longitudinal direction extending from a front region to be arranged on a front side of a wearer toward a rear region to be arranged on a rear side of the wearer, and an article lateral direction orthogonal to the article longitudinal direction, wherein:
the absorbent core is formed of a sheet-like article including a plurality of absorbent units, each of the plurality of absorbent units including
a long base portion having a lateral direction, a longitudinal direction that is longer than the lateral direction, and a thickness direction, and
water-absorbent polymer particles that are fixed to a surface of at least one face of the long base portion,
the absorbent units being arranged such that the absorbent unit's longitudinal direction is oriented in the article longitudinal direction;
the sheet-like article includes a plurality of unit portions arranged in the longitudinal direction, each of the plurality of unit portions including a plurality of the absorbent units arranged side by side in the lateral direction;
the sheet-like article includes
a pair of longitudinal joined regions extending in the longitudinal direction at respective lateral sides which are along the longitudinal direction,
a pair of lateral joined regions extending in the lateral direction at respective end portions in the longitudinal direction, and an intermediate lateral joined region extending in the lateral direction between the lateral joined regions; and the sheet-like article is joined at the longitudinal joined regions, the lateral joined regions, and the intermediate lateral joined region to a constituent member that constitutes the absorbent article and that is adjacent on at least either an upper side or a lower side in the thickness direction, and each of the unit portions includes a section in which neither the upper side nor the lower side thereof in the thickness direction is joined to the constituent member.

2. The absorbent article according to claim 1, wherein:
the unit portions are arranged with a space therebetween in the longitudinal direction;
the intermediate lateral joined region is arranged between the unit portions that are adjacent to one another in the longitudinal direction.

3. The absorbent article according to claim 1, wherein the water-absorbent polymer particles are not arranged in the longitudinal joined regions, the lateral joined regions, and the intermediate lateral joined region.

4. The absorbent article according to claim 1, wherein the longitudinal joined regions extend continuously in the longitudinal direction in the sheet-like article's respective lateral sides which are along the longitudinal direction.

5. The absorbent article according to claim 1, wherein a length, in the lateral direction, of the longitudinal joined region is greater than or equal to a length, in the lateral direction, of the long base portion.

6. The absorbent article according to claim 1, wherein a length, in the longitudinal direction, of the lateral joined region is longer than a length, in the longitudinal direction, of the intermediate lateral joined region.

7. The absorbent article according to claim 1, wherein the constituent member joined to the absorbent core at the longitudinal joined regions, the lateral joined regions, and the intermediate lateral joined region is joined to another constituent member constituting the absorbent article.

8. The absorbent article according to claim 7, wherein elastic members that contract around the wearer's legs are arranged in the other constituent member.

9. The absorbent article according to claim 1, wherein:
the topsheet covers an entire surface of a skin-facing surface of the absorbent core, and includes extension portions extending outward, in the article lateral direction, from respective lateral side edge portions of the absorbent core;
the extension portions are folded back toward a non-skin-facing surface side of the absorbent core and cover the absorbent core's non-skin-facing surface;
a tip-end portion of each of the topsheet's folded-back extension portions is fixed to a constituent member of the absorbent article that is adjacent on the non-skin-facing surface side; and
an elastic member is provided to and arranged along each of the absorbent core's lateral side edge portions, which extend along the longitudinal direction, and contractile force of the respective elastic members causes the absorbent core's lateral side edge portions, which extend along the longitudinal direction, to stand up toward the wearer's skin side.

10. The absorbent article according to claim 1, wherein the unit portions are spaced uniformly in the longitudinal direction.

11. The absorbent article according to claim 1, wherein the absorbent units are arranged so as not to intersect with one another.

12. The absorbent article according to claim 1, wherein the unit portion is formed by using a plurality of the absorbent units, each including the long base portion with a uniform width, and by arranging the absorbent units side by side in the lateral direction and parallel to the longitudinal direction of the sheet-like article.

13. The absorbent article according to claim 1, wherein, in the unit portion, there is no intervening member present between the absorbent units adjacent to one another in the lateral direction of the long base portion.

14. The absorbent article according to claim 1, wherein:
non-slit regions are provided in the sheet-like article; and
the non-slit regions include
a pair of longitudinal non-slit regions extending in the longitudinal direction at the respective lateral sides which are along the longitudinal direction,
a pair of lateral non-slit regions extending in the lateral direction at the respective end portions in the longitudinal direction, and
two intermediate lateral non-slit regions extending in the lateral direction, each being provided between the unit portions adjacent to one another in the longitudinal direction.

15. The absorbent article according to claim 14, wherein the pair of longitudinal joined regions is arranged respectively in the pair of longitudinal non-slit regions on one face and the other face of the sheet-like article.

16. The absorbent article according to claim 15, wherein, in each of the longitudinal joined regions on the one face and the other face, an adhesive is applied along the respective longitudinal non-slit regions.

17. The absorbent article according to claim 16, wherein the adhesive applied to each of the longitudinal non-slit regions is arranged in a manner extending between both end portions, in the longitudinal direction, in each of the longitudinal non-slit regions.

18. The absorbent article according to claim 15, wherein the longitudinal non-slit regions on the one face and the other face each have a non-application portion, in which no adhesive is applied, formed at respective lateral-side outer edges along the longitudinal direction.

19. The absorbent article according to claim 18, wherein the non-application portion is arranged along the longitudinal joined region on the outermost side, in the lateral direction, of the longitudinal joined region.

20. The absorbent article according to claim 18, wherein the non-application portion is arranged substantially parallel to the longitudinal joined region on the outermost side, in the lateral direction, of the longitudinal joined region.

* * * * *